(12) United States Patent
Qiu et al.

(10) Patent No.: US 6,277,814 B1
(45) Date of Patent: Aug. 21, 2001

(54) ENHANCEMENT OF GROWTH IN PLANTS

(75) Inventors: Dewen Qiu, Seattle; Zhong-Min Wei, Kirkland, both of WA (US); Steven V. Beer, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/013,587

(22) Filed: Jan. 26, 1998

Related U.S. Application Data
(60) Provisional application No. 60/036,048, filed on Jan. 27, 1997.

(51) Int. Cl.⁷ .................................................. A01M 27/00
(52) U.S. Cl. ................................ 514/2; 47/58.1; 800/288
(58) Field of Search .............................. 800/250, DIG. 9, 800/DIG. 52, 285, 288, 290; 530/300, 350; 514/2

(56) References Cited

U.S. PATENT DOCUMENTS

| | | |
|---|---|---|
| 4,569,841 | 2/1986 | Liu . |
| 4,597,972 | 7/1986 | Taylor . |
| 4,601,842 | 7/1986 | Caple et al. . |
| 4,740,593 | 4/1988 | Gonzalez et al. . |
| 4,851,223 | 7/1989 | Sampson . |
| 4,886,825 | 12/1989 | Ruess et al. . |
| 4,931,581 | 6/1990 | Schurter et al. . |
| 5,057,422 | 10/1991 | Bol et al. . |
| 5,061,490 | 10/1991 | Paau et al. . |
| 5,135,910 | 8/1992 | Blackburn et al. . |
| 5,173,403 | 12/1992 | Tang . |
| 5,217,950 | 6/1993 | Blackburn et al. . |
| 5,243,038 | 9/1993 | Ferrari et al. . |
| 5,244,658 | 9/1993 | Parke . |
| 5,260,271 | 11/1993 | Blackburn et al. . |
| 5,348,743 | 9/1994 | Ryals et al. . |
| 5,494,684 | 2/1996 | Cohen . |
| 5,523,311 | 6/1996 | Schurter et al. . |
| 5,550,228 | 8/1996 | Godiard et al. . |
| 5,552,527 | 9/1996 | Godiard et al. . |
| 5,850,015 | 12/1998 | Bauer et al. . |
| 6,001,959 | 12/1999 | Bauer et al. . |

FOREIGN PATENT DOCUMENTS

| | | |
|---|---|---|
| 0 612 848 A3 | 8/1994 | (EP) . |
| WO 99/07206 | 2/1989 | (WO) . |
| WO 93/23532 | 11/1993 | (WO) . |
| WO 94/01546 | 1/1994 | (WO) . |
| WO 94/26782 | 11/1994 | (WO) . |
| WO 95/19443 | 7/1995 | (WO) . |
| WO 98/15547 | 4/1998 | (WO) . |
| WO 98/24297 | 6/1998 | (WO) . |
| WO 98/32844 | 7/1998 | (WO) . |
| WO 98/37752 | 9/1998 | (WO) . |
| WO 98/54214 | 12/1998 | (WO) . |
| WO 99/07207 | 2/1999 | (WO) . |

OTHER PUBLICATIONS

Burr et al. Phytopathology. 1978. vol. 68: 1377–1383, 1978.*

Wei et al. Science. 1992. vol. 257: 85–88, 1992.*

He et al. Cell. 1993. vol. 73: 1255–1266, 1993.*

Wengelink et al. J. Bacteriology. 1996. vol. 178: 1061–1069, 1996.*

Barillreul et al. Plant Journal. 1995. vol. 8: 551–560, 1995.*

Klessig and Malamy. Plant Molecular Biology. 1994. Dec. issue. vol. 26: 1439–1458, 1994.*

Alfano et al., "Analysis of the Role of the Pseudomonas syringae pv. Syringae HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19:715–728 (1996).

Linthorst et al., "Constitutive Expression of Pathogenesis–Related Proteins PR–1, GRP, and PR–S in Tobacco Has No Effect on Virus Infection," *The Plant Cell*, 1:285–291 (1989).

Lorang et al., "Characterization of avrE from *Pseudomonas syringae* pv. Tomato: A hrp–Linked Avirulence Locus Consisting Of at Least Two Transcriptional Units," *MPMI* 8:49–57 (1995).

Malamy et al., Salicylic Acid and Plant Disease Resistance, *The Plant Journal*, 2:643–654 (1992).

McGurl et al., "Structure, Expression, and Antisense Inhibition of the Systemin Precursor Gene," *Science*, 255:1570–1573 (1992).

Schulte et al., Expression of the *Xanthomonas campestris* pv. Vesicatoria hrp Gene Cluster, Which Determines Pathogenicity and Hypersensitivity of Pepper and Tomato, Is Plant Inducible, *Journal of Bacteriology*, 174:815–823 (1992).

Wu et al., "Disease Resistance Conferred by Expression of a Gene Encoding $H_2O_2$–Generating Glucose Oxidase in Transgenic Potato Plants," *The Plant Cell*, 7:1357–1368 (1995).

Yu, "Elicitins from Phytophthora and Basic Resistance in Tobacco, " *Proc. Natl. Acad. Sci. USA*, 92:4088–4094 (1995).

(List continued on next page.)

*Primary Examiner*—Gary Benzion
(74) *Attorney, Agent, or Firm*—Nixon Peabody LLP

(57) ABSTRACT

The present invention relates to a method of enhancing growth of plants. This involves applying a hypersensitive response elicitor polypeptide or protein in a non-infectious form to a plant or plant seed under conditions effective to enhance growth of the plant or plants produced from the plant seed. Alternatively, transgenic plants or transgenic plant seeds transformed with a DNA molecule encoding a hypersensitive response elicitor polypeptide or protein can be provided and the transgenic plants or plants resulting from the transgenic plant seeds are grown under conditions effective to enhance plant growth.

35 Claims, 2 Drawing Sheets

OTHER PUBLICATIONS

Nissinen et al., "Clavibacter Michiganensis Subsp. Sepedonicus Elicits a Hypersensitive Response in Tobacco and Secretes Hypersensitive Response–Inducing Protein," *Phytopathology*, 87:678–684 (1997) (Abstract only).

Collmer et al., "*Erwinia chrysanthemi* and *Pseudomonas syringae*: Plant Pathogens Trafficking in Extracellular Virulence Proteins," pp. 43–78.

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).

Preston et al., "The HrpZ Proteins of *Pseudomonas syringae* pvs. *syringae, glycinea*, and *tomato* are Encoded by an Operon Containing *Yersinia ysc* Homologs and Elicit the Hypersensitive Response in Tomato but not Soybean," *Mol. Plant–Microbe Interact.*, 8(5):717–32 (1995).

Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (Jul. 1992).

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Imcompatible Pseudomonas spp. by Blasticidin S, Streptomycin or Elevated Temperature," *Physiological Plant Pathology*, 18:325–37 (1981).

Lerner, R.A., "Tapping the Immunological Repertoire to Produce Antibodies of Predetermined Specificity," *Nature*, 299:592–96 (1982).

Staskawicz et al., "Cloned Avirulence Gene of *Pseudomonas syringae* pv. *glycinea* Determines Race–specific Incompatibility on *Glycine max* (L.) Merr.," *Proc. Natl. Acad. Sci. USA*, 81:6024–28 (1984).

Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).

Huang et al., "Characterization of the hrp Cluster from *Pseudomonas syringae* pv. *syringae* 61 the TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, and Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Microbio.*, 192:79–98 (1994).

Arlat et al., "PopA1, A Protein Which Induces a Hypersensitivity–Like Response on Specific Protein Petunia Gentopyes, is Secreted via the Hrp Pathway of *Pseudomonas solanacearum,*" *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas solanacearum* To Colony Appearance on a Tetrazolium Medium," *Phytopathology*, 44:693–95 (1954).

Winstead et al., "Inoculation Techniques For Evaluating Resistance to *Pseudomonas solanacearum,*" *Phytopathology*, 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant and Soil*, 77:103–13 (1984).

Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).

Atkinson et al., "The Hypersensitive Reaction of Tobacco to *Pseudomonas syringae* pv. *pisi,*" *Plant Physiol.*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease*, 72(1):42–6 (1988).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed), Plenum, NY, 155–64 (1986).

Kloepper et al., "Relationships of in vitro Antibiosis of Plant Growth–Promoting Rhizobacteria to Plant Growth and the Displacement of Root Microflora," *Phytopathology*, 71(10):1020–24 (1981).

Kloepper et al., "Effects of Rhizosphere Colonization by Plant Growth–Promoting Rhizobacteria on Potato Plant Development and Yield," *Phytopathology*, 70(11):1078–82 (1980).

Kloepper et al., "Plant Growth Promotion Mediated by Rhizosphere Bacterial Colonizers," In: *The Rhizosphere and Plant Growth,*—315–32, Keister et al. (eds), pp. 315–326 (1991).

Lifshitz et al., "Growth Promotion of Canola (rapeseed) Seedlings by a Strain of *Pseudomonas putida* Under Gnotobiotic Conditions," Conditions, *Microbiol.* 33:390–95 (1987).

Liu et al., "Induction of Systemic Resistance in Cucumber Against Bacterial Angular Leaf Spot by Plant Growth–Promoting Rhizobacteria," *Phytopathology*, 85(8):843–47 (1995).

Loper et al., "Influence of Bacterial Sources of Indole–3–acetic Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512–22 (1986).

Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425–429 (1987).

Wei et al., "Induction of Systemic Resistance of Cucumber to *Colletotrichum orbiculare* by Select Strains of Plant Growth–Promoting Rhizobacteria," *Phytopathology*, 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186.

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection," *Science*, 250:1002–04 (1990).

Dean et al., "Immunisation Against Disease: The Plant Fights Back," pp. 383–411.

Cameron et al., "Biologically Induced Systemic Acquired Resistance in *Arabidopsis thaliana*," *The Plant Journal*, 5(5):715–25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Micorbiol.*, 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli*," *Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–5 (1991).

Kang et al., "Control of Tomato Mosaic Disease by Interference of an Attenuated Virus," *Res. Rept. RDA (Hort.)*, 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya, Biologiya* 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).

Shields, R., "Towards Insect–Resistant Plants," *Nature*, 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748–56 (1988).

Ricci, et al., "Differential Production of Parasiticein, an Elicitor of Necrosis and Resistance in Tobacco, by Isolates of *Phytophthora parasitica*," *Plant Pathology*, 41:298–307 (1992).

Honée, et al., "Molecular Characterization of the Interaction Between the Fungal Pathogen *Cladosporium fulvum* and Tomato," *Advances in Molecular Genetics of Plant–Microbe Interactions*, 3:199–206 (1994).

Keller, et al., "Responses of Tobacco to Elicitins, Proteins From *Phytophthora spp*. Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi hrp* Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).

Steinberger et al., "Creation and Complementation of Pathogenicity Mutants of *Erwinia amylovora*," *Molecular Plant–Microbe Interactions*, 1(3):135–44 (1988).

Beer et al., "The Hypersensitive Response is Elicited by *Escherichia coli* Containing a Cluster of Pathogenicity Genes from *Erwinia amylovora*," *Phytopathology*, 79(10):1156 (Abstract 169) (1989).

Hiatt et al., "Production of Antibodies in Transgenic Plants," *Nature*, 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).

Huang et al., "Isolation and Purification of a Factor from *Pseudomonas solanacearum* That Induces a Hypersensitive– like Response in Potato Cells," *Molecular Plant–Microbe Interactions*, 2(3):132–38 (1989).

James et al., "Genetic Transformation of Apple (*Malus pumila* Mill.) Using a Disarmed Ti–binary Vector," *Plant Cell Reports*, 7:658–61 (1989).

Laby et al., "Cloning and Preliminary Characterization of an hrp Gene Cluster of *Erwinia amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–98 (1990).

Walters et al., "Gene for Pathogenicity and Ability to Cause the Hypersensitive Reaction Cloned from *Erwinia amylovora*," *Physiological and Molecular Plant Pathology*, 36:509–21 (1990).

Wu et al., "Cloning, Genetic Organization, and Characterization of a Structural Gene Encoding Bacillopeptidase F from *Bacillus subtilis*," *The Journal of Biological Chemistry*, 265(12):6845–50 (1990).

Bauer et al., "Further Characterization of an hrp Gene Cluster of *Erwinia amylovora*," *Molecular Plant–Microbe Interactions*, 4(5):493–99 (1991).

Beer et al., "The hrp Gene Cluster of *Erwinia amylovora*," *Advances in Molecular Genetics of Plant–Microbe Interactions*, 1:53–60 (1991).

Benvenuto et al., "'Phytoantibodies': A General Vector for the Expression of Immunoglobulin Domains in Transgenic Plants," *Plant Molecular Biology*, 17:865–74 (1991).

Milat et al., "Physiological and Structural Changes in Tobacco Leaves Treated with Cryptogein, a Proteinaceous Elicitor from *Phytophthora cryptogea*," *Phytopathology*, 81(11):1364–68 (1991).

Ruberti et al., "A Novel Class of Plant Proteins Containing a Homeodomain with a Closely Linked Leucine Zipper Motif," *The EMBO Journal*, 10(7):1787–91 (1991).

Quigley et al., "Nucleotide Sequence and Expression of a Novel Glycine–Rich Protein Gene from *Arabidopsis thaliana*," *Plant Molecular Biology*, 17:949–52 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1):52–9 (1991).

Waldmann, T.A., "Monoclonal Antibodies in Diagnosis and Therapy," *Science*, 252:1657–62 (1991).

Willis et al., "hrp Genes of Phytopathogenic Bacteria," *Molecular Plant–Microbe Interactions*, 4:(2) 132–38 (1991).

Beer et al., "Are Harpins Universal Elicitors of the Hypersensitive Response of Phytopathogenic Bacteria?," *Advances in Molecular Genetics of Plant–Microbe Interactions*, 2:281–86 (1992).

Laby et al., "Hybridization and Functional Complementation of the hrp Gene Cluster from *Erwinia amylovora* Strain Ea321 with DNA of Other Bacteria," *Molecular Plant–Microbe Interactions*, 5(5):412–19 (1992).

Sandhu, "Protein Engineering of Antibodies," *Crit. Rev. in Biotech.*, 12(5/6):437–62 (1992).

He et al., "*Pseudomonas syringae* pv. *syringae* Harpin$_{Pss}$: A Protein that is Secreted via the Hrp Pathway and Elicits the Hypersensitive Response in Plants," *Cell*, 73:1255–66 (1993).

Bonas, U., "Bacterial Home Goal by Harpins," *Trends in Microbiology*, 2:1–2 (1994).

Boccara, et al., "Plant Defense Elicitor Protein Produced by *Erwinia chrysanthemi*," *Mechanisms of Plant Defense Responses*, p. 166 (1993).

Qui et al., "Treatment of Tomato Seed with Harpin Enhances Germination and Growth and Induces Resistance to *Ralstonia solanacearum*," *Phytopathology*, 87:6, S80 (1997).

Ricci et al., "Proteinaceuos Elicitors of Plant Defense Responses," B. Fritig eds., *Mechanisms of Plant Defense Responses*, Netherlands, pp. 121–130 (1993).

Keen et al., "Syringolide Elicitors Specified By Avirulence Gene D Alleles In *Pseudomonas syringae*," *Advances in Molecular Genetics of Plant–Microbe Interactions*, 3:41–48 (1994).

Bogdanove et al., "Unified Nomenclature For Broadly Conserved hrp Genes of Phytopathogenic Bacteria," *Molecular Microbiology*, 20(3):681–683 (1996).

Bonnet et al., "Acquired Resistance Triggered By Elicitins In Tobacco and Other Plants," *European Journal of Plant Pathology*, 102:181–192 (1996).

Cui et al., "The RsmA$^-$ Mutants of *Erwinia carotovora* subsp. *carotovora* Strain Ecc71 Overexpress hrpN$_{Ecc}$ and Elicit a Hypersensitive Reaction–like Response in Tobacco Leaves," *Molecular Plant–Microbe Interactions*, 9(7):565–573 (1996).

Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell*, 8:1809–1819 (1996).

Wei et al., "Induced Systemic Resistance to Cucumber Dieseases and Increased Plant Growth by Plant Growth–Promoting Rhizobacteria Under Field Conditions," *Phytopathology*, 86:221–224 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance to *Xanthomonas campetris* pv. *oryzae* In Rice," *Physiological and Molecular Plant Pathology*, 51:243–257 (1997).

Kloepper et al., "Enhanced Plant Growth By Siderophores Produced by Plant Growth–Promoting Rhizobacteria," *Nature* 286:885–886 (1980).

* cited by examiner

ENHANCEMENT OF GROWTH IN PLANTS

This application claims the benefit of U.S. Provisional Patent Application Ser. No. 60/036,048, filed Jan. 27, 1997.

This invention was made with support from the U.S. Government under USDA NRI Competitive Research Grant No. 91-37303-6430.

FIELD OF THE INVENTION

The present invention relates to the enhancement of growth in plants.

BACKGROUND OF THE INVENTION

The improvement of plant growth by the application of organic fertilizers has been known and carried out for centuries (H. Marschner, "Mineral Nutrition of Higher Plants," Academic Press: New York pg. 674 (1986). Modern man has developed a complex inorganic fertilizer production system to produce an easy product that growers and farmers can apply to soils or growing crops to improve performance by way of growth enhancement. Plant size, coloration, maturation, and yield may all be improved by the application of fertilizer products. Inorganic fertilizers include such commonly applied chemicals as ammonium nitrate. Organic fertilizers may include animal manures and composted lawn debris, among many other sources.

In most recent years, researchers have sought to improve plant growth through the use of biological products. Insect and disease control agents such as *Beauveria bassiana* and *Trichoderma harizamum* have been registered for the control of insect and disease problems and thereby indirectly improve plant growth and performance (Fravel et al., "Formulation of Microorganisms to Control Plant Diseases," Formulation of Microbial Biopesticides, Beneficial Microorganisms, and Nematodes, H. D. Burges, ed. Chapman and Hall: London (1996).

There is some indication of direct plant growth enhancement by way of microbial application or microbial by-products. Nodulating bacteria have been added to seeds of leguminous crops when introduced to a new site (Weaver et al., "Rhizobium," *Methods of Soil Analysis, Part 2, Chemical and Microbiological Properties*, 2nd ed., American Society of Agronomy: Madison (1982)). These bacteria may improve the nodulation efficiency of the plant and thereby improve the plant's ability to convert free nitrogen into a usable form, a process called nitrogen fixation. Non-leguminous crops do not, as a rule, benefit from such treatment. Added bacteria such as Rhizobium directly parasitize the root hairs, then begin a mutualistic relationship by providing benefit to the plant while receiving protection and sustenance.

Mycorrhizal fungi have also been recognized as necessary microorganisms for optional growth of many crops, especially conifers in nutrient-depleted soils. Mechanisms including biosynthesis of plant hormones (Frankenberger et al., "Biosynthesis of Indole-3-Acetic Acid by the Pine Ectomycorrhizal Fungas *Pisolithus tinctorius*," *Appl. Environ. Microbiol.* 53:2908–13 (1987)), increased uptake of minerals (Harley et al., "The Uptake of Phosphate by Excised Mycorrhizal Roots of Beech," *New Phytologist* 49:388–97 (1950) and Harley et al., "The Uptake of Phosphate by Excised Mycorrhizal Roots of Beech. IV. The Effect of Oxygen Concentration Upon Host and Fungus," *New Phytologist* 52:124–32 (1953)), and water (A. B. Hatch, "The Physical Basis of Mycotrophy in Pinus," *Black Rock Forest Bull.* No. 6, 168 pp. (1937)) have been postulated. Mycorrhizal fungi have not achieved the common frequency of use that modulating bacteria have due to variable and inconsistent results with any given mycorrhizal strain and the difficulty of study of the organisms.

Plant growth-promoting rhizobacteria ("PGPR") have been recognized in recent years for improving plant growth and development. Hypothetical mechanisms range from direct influences (e.g., increased nutrient uptake) to indirect mechanisms (e.g., pathogen displacement). Growth enhancement by application of a PGPR generally refers to inoculation with a live bacterium to the root system and achieving improved growth through bacterium-produced hormonal effects, siderophores, or by prevention of disease through antibiotic production, or competition. In all of the above cases, the result is effected through root colonization, sometimes through the application of seed coatings. There is limited information to suggest that some PGPR strains may be direct growth promoters that enhance root elongation under gnotobiotic conditions (Anderson et al., "Responses of Bean to Root Colonization With *Pseudomonas putida* in a Hydroponic System," *Phytopathology* 75:992–95 (1985), Lifshitz et al., "Growth Promotion of Canola (rapeseed) Seedlings by a Strain of *Pseudomonas putida* Under Gnotobiotic Conditions," *Can. J. Microbiol.* 33:390–95 (1987), Young et al., "PGPR: Is There Relationship Between Plant Growth Regulators and the Stimulation of Plant Growth or Biological Activity?," Promoting Rhizobacteria: Progress and Prospects, Second International Workshop on Plant Growth-promoting Rhizobacteria, pp. 182–86 (1991), Loper et al., "Influence of Bacterial Sources of Indole-3-Acetic Acid on Root Elongation of Sugar Beet," *Phytopathology* 76:386–89 (1986), and Müller et al., "Hormonal Interactions in the Rhizosphere of Maize (*Zea mays* L.) and Their Effect on Plant Development," *Z. Pflanzenernährung Bodenkunde* 152:247–54 (1989); however, the production of plant growth regulators has been proposed as the mechanism mediating these effects. Many bacteria produce various plant growth regulators in vitro (Atzorn et al., "Production of Gibberellins and Indole-3-Acetic Acid by *Rhizobium phaseoli* in Relation to Nodulation of *Phaseolus vulgaris* Roots," *Planta* 175:532–38 (1988) and M. E. Brown, "Plant Growth Substances Produced by Micro-Organism of Solid and Rhizosphere," *J. Appl. Bact.* 35:443–51 (1972)) or antibiotics (Gardner et al., "Growth Promotion and Inhibition by Antibiotic-Producing Fluorescent Pseudomonads on Citrus Roots," *Plant Soil* 77:103–13 (1984)). Siderphore production is another mechanism proposed for some PGPR strains (Ahl et al., "Iron Bound-Siderophores, Cyanic Acid, and Antibiotics Involved in Suppression of *Thievaliopsis basicola* by a *Pseudomonas fluorescens* Strain," *J. Phytopathol.* 116:121–34 (1986), Kloepper et al., "Enhanced Plant Growth by Siderophores Produced by Plant Growth-Promoting Rhizobacteria," *Nature* 286:885–86 (1980), and Kloepper et al., "*Pseudomonas siderophores:* A Mechanism Explaining Disease-Suppressive Soils," *Curr. Microbiol.* 4:317–20 (1980)). The colonization of root surfaces and thus the direct competition with pathogenic bacteria on the surfaces is another mechanism of action (Kloepper et al., "Relationship of in vitro Antibiosis of Plant Growth-Promoting Rhizobacteria to Plant Growth and the Displacement of Root Microflora," *Phytopathology* 71:1020–24 (1981), Weller, et al., "Increased Growth of Wheat by Seed Treatments With Fluorescent Pseudomonads, and Implications of Pythium Control," *Can. J. Microbiol.* 8:328–34 (1986), and Suslow et al., "Rhizobacteria of Sugar Beets: Effects of Seed Application and Root Colonization on Yield," *Phytopathology* 72:199–206 (1982)). Canola (rapeseed) studies have indicated PGPR increased plant growth parameters including yields, seedling emergence and vigor, early-season plant growth (number of leaves and length of main runner), and leaf area (Kloepper et al., "Plant Growth-Promoting Rhizobacteria on Canola (rapeseed)," *Plant Disease* 72:42–46 (1988)). Studies with potato indicated greater yields when Pseudomonas strains were applied to seed potatoes (Burr et al., "Increased Potato Yields by Treatment of Seed Pieces With Specific Strains of Pseudomonas Fluorescens and *P. putida*," *Phytopathology* 68:1377–83 (1978), Kloepper et al., "Effect of Seed Piece Inoculation With Plant Growth-Promoting Rhizobacteria on Populations of *Erwinia carotovora* on Potato Roots and in Daughter Tubers," *Phytopathology* 73:217–19 (1983), Geels et al., "Reduction of Yield Depressions in High Frequency Potato Cropping Soil After Seed Tuber Treatments With Antagonistic Fluorescent Pseudomonas spp.," *Phytopathol. Z.* 108:207–38 (1983), Howie et al., "Rhizobacteria: Influence of Cultivar and Soil Type on Plant Growth and Yield of Potato," *Soil Biol. Biochem.* 15:127–32 (1983), and Vrany et al., "Growth and Yield of Potato Plants Inoculated With Rhizosphere Bacteria," *Folia Microbiol.* 29:248–53 (1984)). Yield increase was apparently due to the competitive effects of the PGPR to eliminate pathogenic bacteria on the seed tuber, possibly by antibiosis (Kloepper et al., "Effect of Seed Piece Inoculation With Plant Growth-Promoting Rhizobacteria on Populations of *Erwinia carotovora* on Potato Roots and in Daughter Tubers," *Phytopathology* 73:217–19 (1983), Kloepper et al., "Effects of Rhizosphere Colonization by Plant Growth-Promoting Rhizobacteria on Potato Plant Development and Yield," *Phytopathology* 70:1078–82 (1980), Kloepper et al., "Emergence-Promoting Rhizobacteria: Description and Implications for Agriculture," pp. 155–164, *Iron, Siderophores, and Plant Disease*, T. R. Swinburne, ed. Plenum, New York (1986), and Kloepper et al., "Relationship of in vitro Antibiosis of Plant Growth-Promoting Rhizobacteria to Plant Growth and the Displacement of Root Microflora," *Phytopathology* 71:1020–24 (1981)). In several studies, plant emergence was improved using PGPR (Tipping et al., "Development of Emergence-Promoting Rhizobacteria for Supersweet Corn," *Phytopathology* 76:938–41 (1990) (abstract) and Kloepper et al., "Emergence-Promoting Rhizobacteria: Description and Implications for Agriculture," pp. 155–164, *Iron, Siderophores, and Plant Disease*, T. R. Swinburne, ed. Plenum, New York (1986)). Numerous other studies indicated improved plant health upon treatment with rhizobacteria, due to biocontrol of plant pathogens (B. Schippers, "Biological Control of Pathogens With Rhizobacteria," *Phil. Trans. R. Soc. Lond. B.* 318:283–93 (1988), Schroth et al., "Disease-Suppressive Soil and Root-Colonizing Bacteria," *Science* 216:1376–81 (1982), Stutz et al., "Naturally Occurring Fluorescent Pseudomonads Involved in Suppression of Black Root Rot of Tobacco," *Phytopathology* 76:181–85 (1986), and D. M. Weller, "Biological Control of Soilborne Plant Pathogens in the Rhizosphere With Bacteria," *Annu. Rev. Phytopathol.* 26:379–407 (1988)).

Pathogen-induced immunization of a plant has been found to promote growth. Injection of *Peronospora tabacina* externally to tobacco xylem not only alleviated stunting but also promoted growth and development. Immunized tobacco plants, in both greenhouse and field experiments, were approximately 40% taller, had a 40% increase in dry weight, a 30% increase in fresh weight, and 4–6 more leaves than control plants (Tuzun, S., et al., "The Effect of Stem Injection with *Peronospora tabacina* and Metalaxyl Treatment on Growth of Tobacco and Protection Against Blue Mould in the Field," *Phytopathology*, 74:804 (1984). These plants flowered approximately 2–3 weeks earlier than control plants (Tuzun, S., et al., "Movement of a Factor in Tobacco Infected with *Peronospora tabacina* Adam which Systemically Protects Against Blue Mould," *Physiological Plant Pathology*, 26:321–30 (1985)).

The present invention is directed to an improvement over prior plant growth enhancement procedures.

SUMMARY OF THE INVENTION

The present invention relates to a method of enhancing growth in plants. This method involves applying a hypersensitive response elicitor polypeptide or protein in a non-infectious form to plants or plant seeds under conditions to impart enhanced growth to the plants or to plants grown from the plant seeds.

As an alternative to applying a hypersensitive response elicitor polypeptide or protein to plants or plant seeds in order to impart enhanced growth to the plants or to plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to enhance growth. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to enhance growth.

The present invention is directed to effecting any form of plant growth enhancement or promotion. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land. It is thus apparent that the present invention constitutes a significant advance in agricultural efficiency.

DETAILED DESCRIPTION OF THE INVENTION

Figure 1:
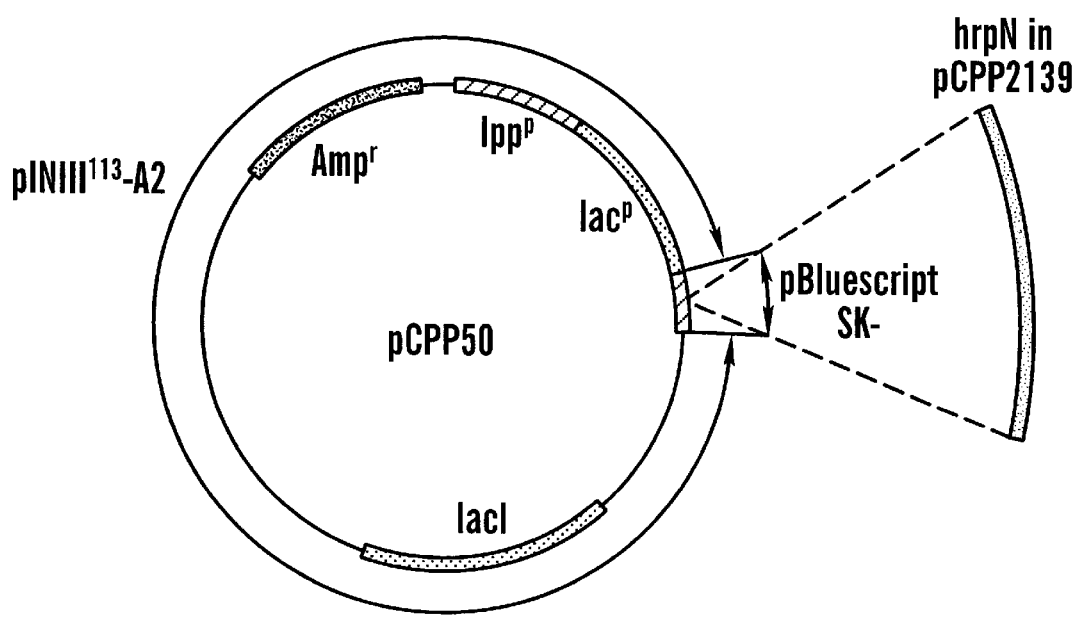
FIG. 1 is a map of plasmid vector pCPP2139 which contains the *Erwinia amylovora* hypersensitive response elicitor gene.
Figure 2:
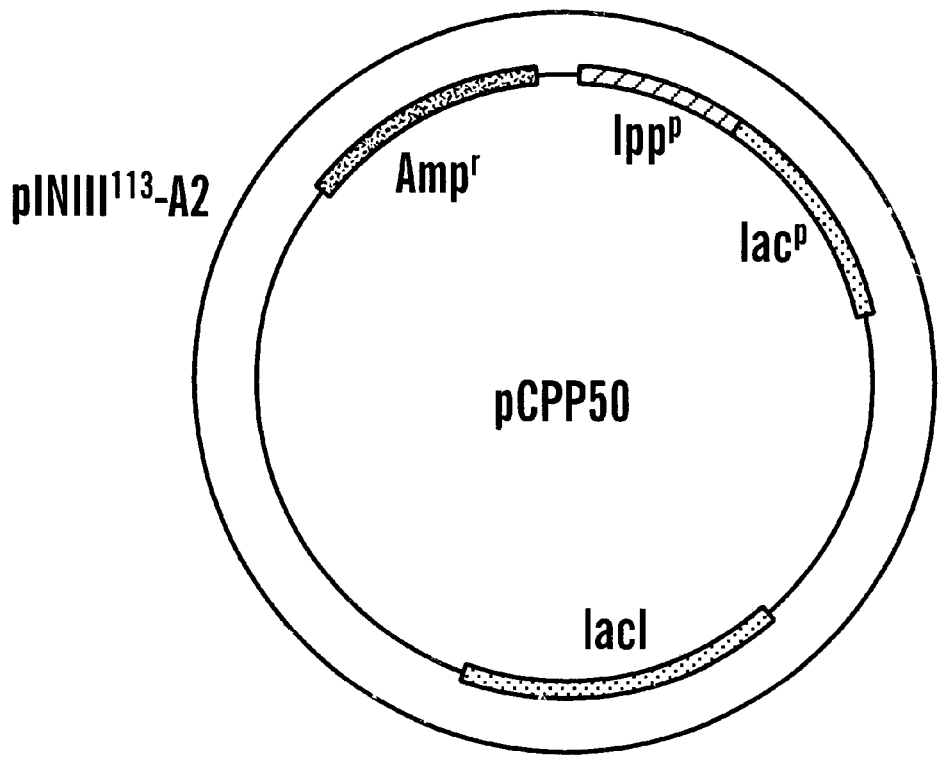
FIG. 2 is a map of plasmid vector pCPP50 which does not contain the *Erwinia amylovora* hypersensitive response elicitor gene but is otherwise the same as plasmid vector pCPP2139 shown in FIG. 1. See Masui, et al., *Bio/Technology* 2:81–85 (1984), which is hereby incorporated by reference.

The present invention relates to a method of enhancing growth in plants. This method involves applying a hypersensitive response elicitor polypeptide or protein in a non-infectious form to all or part of a plant or a plant seed under conditions to impart enhanced growth to the plant or to a plant grown from the plant seed. Alternatively, plants can be treated in this manner to produce seeds, which when planted, impart enhanced growth in progeny plants.

As an alternative to applying a hypersensitive response elicitor polypeptide or protein to plants or plant seeds in order to impart enhanced growth to the plants or to plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to enhance growth. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to enhance growth.

The hypersensitive response elicitor polypeptide or protein utilized in the present invention can correspond to hypersensitive response elicitor polypeptides or proteins derived from a wide variety of fungal and bacterial pathogens. Such polypeptides or proteins are able to elicit local necrosis in plant tissue contacted by the elicitor.

Examples of suitable bacterial sources of polypeptide or protein elicitors include Erwinia, Pseudomonas, and Xanthamonas species (e.g., the following bacteria: Erwinia amylovora, Erwinia chrysanthemi, Erwinia stewartii, Erwinia carotovora, Pseudomonas syringae, Pseudomonas solancearum, Xanthomonas campestris, and mixtures thereof).

An example of a fungal source of a hypersensitive response elicitor protein or polypeptide is Phytophthora. Suitable species of Phytophthora include *Phytophthora pythium, Phytophthora cryptogea, Phytophthora cinnamomi, Phytophthora capsici, Phytophthora megasperma,* and *Phytophthora citrophthora.*

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein. In addition, seeds in accordance with the present invention can be recovered from plants which have been treated with a hypersensitive response elicitor protein or polypeptide in accordance with the present invention.

In one embodiment of the present invention, the hypersensitive response elicitor polypeptides or proteins can be isolated from their corresponding organisms and applied to plants or plant seeds. Such isolation procedures are well known, as described in Arlat, M., F. Van Gijsegem, J. C. Huet, J. C. Pemollet, and C. A. Boucher, "PopA1, a Protein which Induces a Hypersensitive-like Response in Specific Petunia Genotypes is Secreted via the Hrp Pathway of *Pseudomonas solanacearum,*" *EMBO J.* 13:543–553 (1994); He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993); and Wei, Z.-M., R. J. Laby, C. H. Zumoff, D. W. Bauer, S.-Y. He, A. Collmer, and S. V. Beer, "Harpin Elicitor of the Hypersensitive Response Produced by the Plant Pathogen *Erwinia amylovora, Science* 257:85–88 (1992), which are hereby incorporated by reference. See also pending U.S. patent application Ser. Nos. 08/200,724 and 08/062,024, which are hereby incorporated by reference. Preferably, however, the isolated hypersensitive response elicitor polypeptides or proteins of the present invention are produced recombinantly and purified as described below.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seeds cells. In these embodiments, the hypersensitive response elicitor polypeptide or protein is produced by the bacteria in Planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli,* which does not elicit a hypersensitive response in plants, can be transformed with genes encoding a hypersensitive response elicitor polypeptide or protein and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato plants or seeds to enhance growth without causing disease in that species.

The hypersensitive response elicitor polypeptide or protein from *Erwinia chrysanthemi* has an amino acid sequence corresponding to SEQ. ID. No. 1 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
                20                  25                  30
```

-continued

```
Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
                100                 105                 110

Leu Leu Gly His Asp Thr Val Thr Lys Leu Thr Asn Gln Ser Asn Gln
            115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
                180                 185                 190

Gly Asn Ala Ile Gly Met Gly Val Gly Gln Asn Ala Ala Leu Ser Ala
            195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
                260                 265                 270

Pro Asp Asp Asp Gly Met Thr Gly Ala Ser Met Asp Lys Phe Arg Gln
            275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 2 as follows:

```
CGATTTTACC CGGGTGAACG TGCTATGACC GACAGCATCA CGGTATTCGA CACCGTTACG    60

GCGTTTATGG CCGCGATGAA CCGGCATCAG GCGGCGCGCT GGTCGCCGCA ATCCGGCGTC   120

GATCTGGTAT TTCAGTTTGG GGACACCGGG CGTGAACTCA TGATGCAGAT TCAGCCGGGG   180

CAGCAATATC CCGGCATGTT GCGCACGCTG CTCGCTCGTC GTTATCAGCA GGCGGCAGAG   240

TGCGATGGCT GCCATCTGTG CCTGAACGGC AGCGATGTAT TGATCCTCTG GTGGCCGCTG   300

CCGTCGGATC CCGGCAGTTA TCCGCAGGTG ATCGAACGTT TGTTTGAACT GGCGGGAATG   360
```

-continued

```
ACGTTGCCGT CGCTATCCAT AGCACCGACG GCGCGTCCGC AGACAGGGAA CGGACGCGCC    420

CGATCATTAA GATAAAGGCG GCTTTTTTTA TTGCAAAACG GTAACGGTGA GGAACCGTTT    480

CACCGTCGGC GTCACTCAGT AACAAGTATC CATCATGATG CCTACATCGG GATCGGCGTG    540

GGCATCCGTT GCAGATACTT TTGCGAACAC CTGACATGAA TGAGGAAACG AAATTATGCA    600

AATTACGATC AAAGCGCACA TCGGCGGTGA TTTGGGCGTC TCCGGTCTGG GGCTGGGTGC    660

TCAGGGACTG AAAGGACTGA ATTCCGCGGC TTCATCGCTG GGTTCCAGCG TGGATAAACT    720

GAGCAGCACC ATCGATAAGT TGACCTCCGC GCTGACTTCG ATGATGTTTG GCGGCGCGCT    780

GGCGCAGGGG CTGGGCGCCA GCTCGAAGGG GCTGGGGATG AGCAATCAAC TGGGCCAGTC    840

TTTCGGCAAT GGCGCGCAGG GTGCGAGCAA CCTGCTATCC GTACCGAAAT CCGGCGGCGA    900

TGCGTTGTCA AAAATGTTTG ATAAAGCGCT GGACGATCTG CTGGGTCATG ACACCGTGAC    960

CAAGCTGACT AACCAGAGCA ACCAACTGGC TAATTCAATG CTGAACGCCA GCCAGATGAC   1020

CCAGGGTAAT ATGAATGCGT TCGGCAGCGG TGTGAACAAC GCACTGTCGT CCATTCTCGG   1080

CAACGGTCTC GGCCAGTCGA TGAGTGGCTT CTCTCAGCCT TCTCTGGGGG CAGGCGGCTT   1140

GCAGGGCCTG AGCGGCGCGG GTGCATTCAA CCAGTTGGGT AATGCCATCG GCATGGGCGT   1200

GGGGCAGAAT GCTGCGCTGA GTGCGTTGAG TAACGTCAGC ACCCACGTAG ACGGTAACAA   1260

CCGCCACTTT GTAGATAAAG AAGATCGCGG CATGGCGAAA GAGATCGGCC AGTTTATGGA   1320

TCAGTATCCG GAAATATTCG GTAAACCGGA ATACCAGAAA GATGGCTGGA GTTCGCCGAA   1380

GACGGACGAC AAATCCTGGG CTAAAGCGCT GAGTAAACCG GATGATGACG GTATGACCGG   1440

CGCCAGCATG GACAAATTCC GTCAGGCGAT GGGTATGATC AAAAGCGCGG TGGCGGGTGA   1500

TACCGGCAAT ACCAACCTGA ACCTGCGTGG CGCGGGCGGT GCATCGCTGG GTATCGATGC   1560

GGCTGTCGTC GGCGATAAAA TAGCCAACAT GTCGCTGGGT AAGCTGGCCA ACGCCTGATA   1620

ATCTGTGCTG GCCTGATAAA GCGGAAACGA AAAAGAGAC GGGGAAGCCT GTCTCTTTTC    1680

TTATTATGCG GTTTATGCGG TTACCTGGAC CGGTTAATCA TCGTCATCGA TCTGGTACAA   1740

ACGCACATTT TCCCGTTCAT TCGCGTCGTT ACGCGCCACA ATCGCGATGG CATCTTCCTC   1800

GTCGCTCAGA TTGCGCGGCT GATGGGGAAC GCCGGGTGGA ATATAGAGAA ACTCGCCGGC   1860

CAGATGGAGA CACGTCTGCG ATAAATCTGT GCCGTAACGT GTTTCTATCC GCCCCTTTAG   1920

CAGATAGATT GCGGTTTCGT AATCAACATG GTAATGCGGT TCCGCCTGTG CGCCGGCCGG   1980

GATCACCACA ATATTCATAG AAAGCTGTCT TGCACCTACC GTATCGCGGG AGATACCGAC   2040

AAAATAGGGC AGTTTTTGCG TGGTATCCGT GGGGTGTTCC GGCCTGACAA TCTTGAGTTG   2100

GTTCGTCATC ATCTTTCTCC ATCTGGGCGA CCTGATCGGT T                       2141
```

The hypersensitive response elicitor polypeptide or protein derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
 1               5                  10                  15

Ile Gly Gly Ala Gly Gly Asn Asn Gly Leu Leu Gly Thr Ser Arg Gln
                20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60
```

-continued

```
Met Met Met Ser Met Met Gly Gly Gly Gly Leu Met Gly Gly Gly Leu
65              70                  75                  80

Gly Gly Gly Leu Gly Asn Gly Leu Gly Gly Ser Gly Gly Leu Gly Glu
                85              90                  95

Gly Leu Ser Asn Ala Leu Asn Asp Met Leu Gly Gly Ser Leu Asn Thr
            100             105             110

Leu Gly Ser Lys Gly Gly Asn Asn Thr Thr Ser Thr Thr Asn Ser Pro
            115             120             125

Leu Asp Gln Ala Leu Gly Ile Asn Ser Thr Ser Gln Asn Asp Asp Ser
    130             135             140

Thr Ser Gly Thr Asp Ser Thr Ser Asp Ser Ser Asp Pro Met Gln Gln
145             150             155             160

Leu Leu Lys Met Phe Ser Glu Ile Met Gln Ser Leu Phe Gly Asp Gly
                165             170             175

Gln Asp Gly Thr Gln Gly Ser Ser Ser Gly Lys Gln Pro Thr Glu
            180             185             190

Gly Glu Gln Asn Ala Tyr Lys Lys Gly Val Thr Asp Ala Leu Ser Gly
            195             200             205

Leu Met Gly Asn Gly Leu Ser Gln Leu Leu Gly Asn Gly Gly Leu Gly
    210             215             220

Gly Gly Gln Gly Gly Asn Ala Gly Thr Gly Leu Asp Gly Ser Ser Leu
225             230             235             240

Gly Gly Lys Gly Leu Gln Asn Leu Ser Gly Pro Val Asp Tyr Gln Gln
            245             250             255

Leu Gly Asn Ala Val Gly Thr Gly Ile Gly Met Lys Ala Gly Ile Gln
            260             265             270

Ala Leu Asn Asp Ile Gly Thr His Arg His Ser Ser Thr Arg Ser Phe
    275             280             285

Val Asn Lys Gly Asp Arg Ala Met Ala Lys Glu Ile Gly Gln Phe Met
    290             295             300

Asp Gln Tyr Pro Glu Val Phe Gly Lys Pro Gln Tyr Gln Lys Gly Pro
305             310             315             320

Gly Gln Glu Val Lys Thr Asp Asp Lys Ser Trp Ala Lys Ala Leu Ser
            325             330             335

Lys Pro Asp Asp Asp Gly Met Thr Pro Ala Ser Met Glu Gln Phe Asn
            340             345             350

Lys Ala Lys Gly Met Ile Lys Arg Pro Met Ala Gly Asp Thr Gly Asn
            355             360             365

Gly Asn Leu Gln Ala Arg Gly Ala Gly Ser Ser Leu Gly Ile Asp
    370             375             380

Ala Met Met Ala Gly Asp Ala Ile Asn Asn Met Ala Leu Gly Lys Leu
385             390             395             400

Gly Ala Ala
```

This hypersensitive response elicitor polypeptide or protein has a molecular weight of about 39 kDa, has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," Science 257:85–88 (1992), which is hereby incorporated by reference. The DNA molecule encoding this polypeptide or protein has a nucleotide sequence corresponding to SEQ. ID. No. 4 as follows:

```
AAGCTTCGGC ATGGCACGTT TGACCGTTGG GTCGGCAGGG TACGTTTGAA TTATTCATAA     60
GAGGAATACG TTATGAGTCT GAATACAAGT GGGCTGGGAG CGTCAACGAT GCAAATTTCT    120
ATCGGCGGTG CGGGCGGAAA TAACGGGTTG CTGGGTACCA GTCGCCAGAA TGCTGGGTTG    180
GGTGGCAATT CTGCACTGGG GCTGGGCGGC GGTAATCAAA ATGATACCGT CAATCAGCTG    240
GCTGGCTTAC TCACCGGCAT GATGATGATG ATGAGCATGA TGGGCGGTGG TGGGCTGATG    300
GGCGGTGGCT TAGGCGGTGG CTTAGGTAAT GGCTTGGGTG GCTCAGGTGG CCTGGGCGAA    360
GGACTGTCGA ACGCGCTGAA CGATATGTTA GGCGGTTCGC TGAACACGCT GGGCTCGAAA    420
GGCGGCAACA ATACCACTTC AACAACAAAT TCCCCGCTGG ACCAGGCGCT GGGTATTAAC    480
TCAACGTCCC AAAACGACGA TTCCACCTCC GGCACAGATT CCACCTCAGA CTCCAGCGAC    540
CCGATGCAGC AGCTGCTGAA GATGTTCAGC GAGATAATGC AAAGCCTGTT TGGTGATGGG    600
CAAGATGGCA CCCAGGGCAG TTCCTCTGGG GGCAAGCAGC CGACCGAAGG CGAGCAGAAC    660
GCCTATAAAA AAGGAGTCAC TGATGCGCTG TCGGGCCTGA TGGGTAATGG TCTGAGCCAG    720
CTCCTTGGCA ACGGGGGACT GGGAGGTGGT CAGGGCGGTA ATGCTGGCAC GGGTCTTGAC    780
GGTTCGTCGC TGGGCGGCAA AGGGCTGCAA AACCTGAGCG GGCCGGTGGA CTACCAGCAG    840
TTAGGTAACG CCGTGGGTAC CGGTATCGGT ATGAAAGCGG GCATTCAGGC GCTGAATGAT    900
ATCGGTACGC ACAGGCACAG TTCAACCCGT TCTTTCGTCA ATAAAGGCGA TCGGGCGATG    960
GCGAAGGAAA TCGGTCAGTT CATGGACCAG TATCCTGAGG TGTTTGGCAA GCCGCAGTAC   1020
CAGAAAGGCC CGGGTCAGGA GGTGAAAACC GATGACAAAT CATGGGCAAA AGCACTGAGC   1080
AAGCCAGATG ACGACGGAAT GACACCAGCC AGTATGGAGC AGTTCAACAA AGCCAAGGGC   1140
ATGATCAAAA GGCCCATGGC GGGTGATACC GGCAACGGCA ACCTGCAGGC ACGCGGTGCC   1200
GGTGGTTCTT CGCTGGGTAT TGATGCCATG ATGGCCGGTG ATGCCATTAA CAATATGGCA   1260
CTTGGCAAGC TGGGCGCGGC TTAAGCTT                                      1288
```

The hypersensitive response elicitor polypeptide or protein derived from *Pseudomonas syringae* has an amino acid sequence corresponding to SEQ. ID. No. 5 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
```

```
                  -continued
145                 150                 155                 160
Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
                260                 265                 270

Asn Thr Pro Gln Thr Gly Thr Ser Ala Asn Gly Gly Gln Ser Ala Gln
            275                 280                 285

Asp Leu Asp Gln Leu Leu Gly Gly Leu Leu Leu Lys Gly Leu Glu Ala
        290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 6 as follows:

```
ATGCAGAGTC TCAGTCTTAA CAGCAGCTCG CTGCAAACCC CGGCAATGGC CCTTGTCCTG    60
GTACGTCCTG AAGCCGAGAC GACTGGCAGT ACGTCGAGCA AGGCGCTTCA GGAAGTTGTC   120
GTGAAGCTGG CCGAGGAACT GATGCGCAAT GGTCAACTCG ACGACAGCTC GCCATTGGGA   180
AAACTGTTGG CCAAGTCGAT GGCCGCAGAT GGCAAGGCGG GCGGCGGTAT TGAGGATGTC   240
ATCGCTGCGC TGGACAAGCT GATCCATGAA AAGCTCGGTG ACAACTTCGG CGCGTCTGCG   300
GACAGCGCCT CGGGTACCGG ACAGCAGGAC CTGATGACTC AGGTGCTCAA TGGCCTGGCC   360
AAGTCGATGC TCGATGATCT TCTGACCAAG CAGGATGGCG GGACAAGCTT CTCCGAAGAC   420
GATATGCCGA TGCTGAACAA GATCGCGCAG TTCATGGATG ACAATCCCGC ACAGTTTCCC   480
AAGCCGGACT CGGGCTCCTG GGTGAACGAA CTCAAGGAAG ACAACTTCCT TGATGGCGAC   540
GAAACGGCTG CGTTCCGTTC GGCACTCGAC ATCATTGGCC AGCAACTGGG TAATCAGCAG   600
AGTGACGCTG GCAGTCTGGC AGGGACGGGT GGAGGTCTGG GCACTCCGAG CAGTTTTTCC   660
AACAACTCGT CCGTGATGGG TGATCCGCTG ATCGACGCCA ATACCGGTCC CGGTGACAGC   720
GGCAATACCC GTGGTGAAGC GGGGCAACTG ATCGGCGAGC TTATCGACCG TGGCCTGCAA   780
TCGGTATTGG CCGGTGGTGG ACTGGGCACA CCCGTAAACA CCCCGCAGAC CGGTACGTCG   840
GCGAATGGCG GACAGTCCGC TCACGATCTT GATCAGTTCC TGGGCGGCTT GCTGCTCAAG   900
```

-continued

```
GGCCTGGAGG CAACGCTCAA GGATGCCGGG CAAACAGGCA CCGACGTGCA GTCGAGCGCT    960

GCGCAAATCG CCACCTTGCT GGTCAGTACG CTGCTGCAAG GCACCCGCAA TCAGGCTGCA   1020

GCCTGA                                                              1026
```

The hypersensitive response elicitor polypeptide or protein derived from *Pseudomonas solanacearum* has an amino acid sequence corresponding to SEQ. ID. No. 7 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

It is encoded by a DNA molecule having a nucleotide sequence corresponding SEQ. ID. No. 8 as follows:

```
ATGTCAGTCG GAAACATCCA GAGCCCGTCG AACCTCCCGG GTCTGCAGAA CCTGAACCTC    60

AACACCAACA CCAACAGCCA GCAATCGGGC CAGTCCGTGC AAGACCTGAT CAAGCAGGTC   120

GAGAAGGACA TCCTCAACAT CATCGCAGCC CTCGTGCAGA AGGCCGCACA GTCGGCGGGC   180

GGCAACACCG GTAACACCGG CAACGCGCCG GCGAAGGACG GCAATGCCAA CGCGGGCGCC   240

AACGACCCGA GCAAGAACGA CCCGAGCAAG AGCCAGGCTC CGCAGTCGGC CAACAAGACC   300

GGCAACGTCG ACGACGCCAA CAACCAGGAT CCGATGCAAG CGCTGATGCA GCTGCTGGAA   360

GACCTGGTGA AGCTGCTGAA GGCGGCCCTG CACATGCAGC AGCCCGGCGG CAATGACAAG   420

GGCAACGGCG TGGGCGGTGC CAACGGCGCC AAGGGTGCCG GCGGCCAGGG CGGCCTGGCC   480

GAAGCGCTGC AGGAGATCGA GCAGATCCTC GCCCAGCTCG GCGGCGGCGG TGCTGGCGCC   540

GGCGGCGCGG GTGGCGGTGT CGGCGGTGCT GGTGGCGCGG ATGGCGGCTC CGGTGCGGGT   600

GGCGCAGGCG GTGCGAACGG CGCCGACGGC GGCAATGGCG TGAACGGCAA CCAGGCGAAC   660

GGCCCGCAGA ACGCAGGCGA TGTCAACGGT GCCAACGGCG CGGATGACGG CAGCGAAGAC   720

CAGGGCGGCC TCACCGGCGT GCTGCAAAAG CTGATGAAGA TCCTGAACGC GCTGGTGCAG   780

ATGATGCAGC AAGGCGGCCT CGGCGGCGGC AACCAGGCGC AGGGCGGCTC GAAGGGTGCC   840

GGCAACGCCT CGCCGGCTTC CGGCGCGAAC CCGGGCGCGA ACCAGCCCGG TTCGGCGGAT   900

GATCAATCGT CCGGCCAGAA CAATCTGCAA TCCCAGATCA TGGATGTGGT GAAGGAGGTC   960

GTCCAGATCC TGCAGCAGAT GCTGGCGGCG CAGAACGGCG GCAGCCAGCA GTCCACCTCG  1020

ACGCAGCCGA TGTAA                                                   1035
```

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum*," *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ. ID. No. 9 as follows:

```
Thr Leu Ile Glu Leu Met Ile Val Val Ala Ile Ile Ala Ile Leu Ala
1               5                   10                  15
Ala Ile Ala Leu Pro Ala Tyr Gln Asp Tyr
            20                  25
```

This sequence is an amino terminal sequence having 26 residues only from the hypersensitive response elicitor polypeptide or protein of *Xanthomonas campestris* pv. glycines. It matches with fimbrial subunit proteins determined in other *Xanthomonas campestris* pathovars.

The hypersensitive response elicitor polypeptide or protein from *Xanthomonas campestris* pv. pelargonii is heat stable, protease sensitive, and has a molecular weight of 20 kDa. It includes an amino acid sequence corresponding to SEQ. ID. No. 10 as follows:

```
Ser Ser Gln Gln Ser Pro Ser Ala Gly Ser Glu Gln Gln Leu Asp Gln
1               5                   10                  15
Leu Leu Ala Met
            20
```

Isolation of *Erwinia carotovora* hypersensitive response elictor protein or polypeptide is described in Cui et al., "The RsmA Mutants of *Erwinia carotovora* subsp. carotovora Strain Ecc71Overexpress hrp $N_{ECC}$ and Elicit a Hypersensitive Reaction-like Response in Tobacco Leaves," *MPMI*, 9(7):565–73 (1996), which is hereby incorporated by reference. The hypersensitive response elicitor proptein or polypeptide is shown in Ahmad et al., "Harpin is Not Necessary for the Pathogenicity of *Erwinia stewartii* on Maize," *8th Int'l. Cong. Molec. Plant-Microbe Interact.*, July 14–19, 1996 and Ahmad, et al., "Harpin is Not Necessary for the Pathogenicity of *Erwinia stewartii* on Maize," *Ann. Mtq. Am. Phytopath. Soc.*, July 27–31, 1996, which are hereby incorporated by reference.

Hypersensitive response elicitor proteins or polypeptides from *Phytophthora parasitica*, *Phytophthora cryptogea*, *Phytophthora cinnamoni*, *Phytophthora capsici*, *Phytophthora megasperma*, and *Phytophora citrophthora* are described in Kaman, et al., "Extracellular Protein Elicitors from Phytophthora: Most Specificity and Induction of Resistance to Bacterial and Fungal Phytopathogens," *Molec. Plant-Microbe Interact.*, 6(1):15–25 (1993), Ricci et al., "Structure and Activity of Proteins from Pathogenic Fungi Phytophthora Eliciting Necrosis and Acquired Resistance in Tobacco," *Eur. J. Biochem.*, 183:555–63 (1989), Ricci et al., "Differential Production of Parasiticein, and Elicitor of Necrosis and Resistance in Tobacco, by Isolates of *Phytophthora parasitica*," *Plant Path.* 41:298–307 (1992), Baillreul et al, "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *Plant J.*, 8(4):551–60 (1995), and Bonnet et al., "Acquired Resistance Triggered by Elicitors in Tobacco and Other Plants," *Eur. J. Plant Path.*, 102:181–92 (1996), which are hereby incorporated by reference.

The above elicitors are exemplary. Other elicitors can be identified by growing fungi or bacteria that elicit a hypersensitive response under which genes encoding an elicitor are expressed. Cell-free preparations from culture supernatants can be tested for elicitor activity (i.e. local necrosis) by using them to infiltrate appropriate plant tissues.

It is also possible to use fragments of the above hypersensitive response elicitor polypeptides or proteins as well as fragments of full length elicitors from other pathogens, in the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or a peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increase and expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of a useful fragment is the popA1 fragment of the hypersensitive response elicitor polypeptide or protein from *Pseudomonas solanacearum*. See Arlat, M., F. Van Gijsegem, J. C. Huet, J. C. Pernollet, and C. A. Boucher, "PopA1, a Protein Which Induces a Hypersensitive-like Response in Specific Petunia Genotypes is Secreted via the Hrp Pathway of *Pseudomonas solanacearum*," *EMBO J.* 13:543–53 (1994), which is hereby incorporated by reference. As to *Erwinia amylovora*, a suitable fragment can be, for example, either or both the polypeptide extending between and including amino acids 1 and 98 of SEQ. ID. No. 3 and the polypeptide extending between and including amino acids 137 and 204 of SEQ. ID. No. 3.

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide.

The protein or polypeptide of the present invention is preferably produced in purified form (preferably at least about 60%, more preferably 80%, pure) by conventional techniques. Typically, the protein or polypeptide of the present invention is produced but not secreted into the growth medium of recombinant host cells. Alternatively, the protein or polypeptide of the present invention is secreted into growth medium. In the case of unsecreted protein, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the hypersensitive response elicitor protein is separated by centrifugation. The supernatant fraction containing the polypeptide or protein of the present invention is subjected to gel filtration in an appropriately sized dextran or polyacrylamide column to separate the proteins. If necessary, the protein fraction may be further purified by ion exchange or HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The method of the present invention can be utilized to treat a wide variety of plants or their seeds to enhance growth. Suitable plants include dicots and monocots. More particularly, useful crop plants can include: rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane. Examples of suitable ornamental plants are: rose, Saintpaulia, petunia, pelargonium, poinsettia, chrysanthemum, carnation, and zinnia.

The method of the present invention involving application of the hypersensitive response elicitor polypeptide or protein can be carried out through a variety of procedures when all or part of the plant is treated, including leaves, stems, roots, etc. This may (but need not) involve infiltration of the hypersensitive response elicitor polypeptide or protein into the plant. Suitable application methods include topical application (e.g., high or low pressure spraying), injection, dusting, and leaf abrasion proximate to when elicitor application takes place. When treating plant seeds, in accordance with the application embodiment of the present invention, the hypersensitive response elicitor protein or polypeptide can be applied by topical application (low or high pressure spraying), coating, immersion, dusting, or injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to enhance growth in the plants. Such propagated plants may, in turn, be useful in producing seeds or propagules (e.g., cuttings) that produce plants capable of enhanced growth.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 0.5 nM hypersensitive response elicitor polypeptide or protein.

Although not required, this composition may contain additional additives including fertilizer, insecticide, fungicide, nematacide, herbicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art, such as by biolistics or Agrobacterium mediated transformation. Examples of suitable hypersensitive response elicitor polypeptides or proteins and the nucleic acid sequences for their encoding DNA are disclosed supra. Once transgenic plants of this type are produced, the plants themselves can be cultivated in accordance with conventional procedure with the presence of the gene encoding the hypersensitive response elicitor resulting in enhanced growth of the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart enhanced growth. While not wishing to be bound by theory, such growth enhancement may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, dusting, and immersion. Similarly, after plants have been propagated from the transgenic plant seeds, the plants may be treated with one or more applications of the hypersensitive response elicitor to enhance plant growth. Such plants may also be treated with conventional plant treatment agents (e.g., insecticides, fertilizers, etc.). The transgenic plants of the present invention are useful in producing seeds or propagules (e.g., cuttings) from which plants capable of enhanced growth would be produced.

EXAMPLES

Example 1

Effect of Treating Tomato Seeds with *Erwinia amylovora* Hypersensitive Response Elicitor on Germination Percentage Seeds of the Marglobe Tomato Variety were submerged in 40 ml of *Erwinia amylovora* hypersensitive response elicitor solution ("harpin"). Harpin was prepared by growing *E. coli* strain DH5 containing the plasmid pCPP2139 (see FIG. 1), lysing the cells by sonication, heat treating by holding in boiling water for 5 minutes before centrifuging to remove cellular debris, and precipitating proteins and other heat-labile components. The resulting preparation ("CFEP") was diluted serially. These dilutions (1:40, 1:80, 1:160, 1:320 and 1:640) contained 20, 10, 5, 2.5, and 1.25 μgm/ml, respectively, of harpin based on Western Blot assay. Seeds were soaked in harpin or buffer in beakers on day 0 for 24 hours at 28° C. in a growth chamber. After soaking, the seeds were sown in germination pots with artificial soil on day 1. This procedure was carried out on 100 seeds per treatment.

Treatments:

1. Seeds in harpin (1:40) (20 μgm/ml).
2. Seeds in harpin (1:80) (10 μgm/ml).
3. Seeds in harpin (1:160) (5 μgm/ml).
4. Seeds in harpin (1:320) (2.5 μgm/ml).
5. Seeds in harpin (1:640) (1.25 μgm/ml).
6. Seeds in buffer (5 mM $KPO_4$, pH 6.8).

TABLE 1

Number of Seedlings After Seed Treatment

| Treatment | | Number of seeds germinated | | |
|---|---|---|---|---|
| Day 0 | Day 1 | Day 5 | Day 7 | Day 9 |
| Harpin seed soak (20 μgm/ml) | sowing | 43 | 57 | 59 |
| Harpin seed soak (10 μgm/ml) | sowing | 43 | 52 | 52 |
| Harpin seed soak (5 μgm/ml) | sowing | 40 | 47 | 51 |
| Harpin seed soak (2.5 μgm/ml) | sowing | 43 | 56 | 58 |
| Harpin seed soak (1.25 μgm/ml) | sowing | 38 | 53 | 57 |
| Buffer seed soak | sowing | 27 | 37 | 40 |

As shown in Table 1, the treatment of tomato seeds with *Erwinia amylovora* hypersensitive response elicitor reduced the time needed for germination and greatly increased the percentage of germination.

Example 2
Effect of Treating Tomato Seeds with *Erwinia amylovora* Hypersensitive Response Elicitor on Tomato Plant Height Seeds of the Marglobe Tomato Variety were submerged in *Erwinia amylovora* harpin (1:15, 1:30, 1:60, and 1:120) or buffer in beakers on day 0 for 24 hours at 28° C. in a growth chamber. After soaking, the seeds were sown in germination pots with artificial soil on day 1.

Ten uniform appearing plants per treatment were chosen randomly and measured. The seedlings were measured by ruler from the surface of soil to the top of plant.

Treatments:

1. Harpin (1:15) (52 μgm/ml).
2. Harpin (1:30) (26 μgm/ml).
3. Harpin (1:60) (13 μgm/ml).
4. Harpin (1:120) (6.5 μgm/ml).
5. Buffer (5 mM $KPO_4$, pH 6.8).

TABLE 2

Seedling Height (cm) 15 Days After Seed Treatment.

| Treat | Plants | 1 | 2 | 3 | 4 | 5 | 6 | 7 | 8 | 9 | 10 | Mean |
|---|---|---|---|---|---|---|---|---|---|---|---|---|
| 52 μgm/ml | 10 | 5.6 | 5.8 | 5.8 | 5.6 | 6.0 | 6.0 | 5.8 | 5.4 | 5.8 | 5.6 | 5.7 |
| 26 μgm/ml | 10 | 6.8 | 7.2 | 6.6 | 7.0 | 6.8 | 6.8 | 7.0 | 7.4 | 7.2 | 7.0 | 7.0 |
| 13 μgm/ml | 10 | 5.8 | 5.6 | 6.0 | 5.6 | 5.8 | 5.8 | 5.6 | 5.8 | 6.0 | 5.6 | 5.9 |
| 6.5 μgm/ml | 10 | 5.4 | 5.2 | 5.6 | 5.4 | 5.2 | 5.4 | 5.6 | 5.6 | 5.4 | 5.2 | 5.4 |
| Buffer | 10 | 5.6 | 5.4 | 5.2 | 5.2 | 5.4 | 5.2 | 5.0 | 5.2 | 5.4 | 5.6 | 5.3 |

TABLE 3

Seedling Height (cm) 21 Days After Seed Treatment.

| Treat | Plants | 1 | 2 | 3 | 4 | 5 | 6 | 7 | 8 | 9 | 10 | Mean |
|---|---|---|---|---|---|---|---|---|---|---|---|---|
| 52 μgm/ml | 10 | 7.6 | 7.8 | 7.6 | 7.6 | 7.8 | 7.8 | 7.8 | 7.4 | 7.6 | 7.6 | 7.7 |
| 26 μgm/ml | 10 | 8.2 | 8.2 | 8.0 | 9.0 | 8.4 | 8.6 | 8.6 | 9.0 | 9.2 | 9.0 | 8.6 |
| 13 μgm/ml | 10 | 6.8 | 6.6 | 6.8 | 6.8 | 6.8 | 6.8 | 6.6 | 7.2 | 7.0 | 7.2 | 6.9 |
| 6.5 μgm/ml | 10 | 6.8 | 6.6 | 6.6 | 6.4 | 6.8 | 6.6 | 6.8 | 6.6 | 6.6 | 6.8 | 6.7 |
| Buffer | 10 | 6.6 | 6.4 | 6.2 | 6.6 | 6.4 | 6.6 | 6.8 | 6.4 | 6.4 | 6.6 | 6.5 |

TABLE 4

Seedling Height (cm) 27 Days After Seed Treatment.

| Treat | 1 | 2 | 3 | 4 | 5 | 6 | 7 | 8 | 9 | 10 | Mean |
|---|---|---|---|---|---|---|---|---|---|---|---|
| 52 μgm/ml | 10.2 | 10.6 | 10.4 | 10.6 | 10.4 | 10.6 | 10.8 | 10.4 | 10.8 | 10.6 | 10.5 |
| 26 μgm/ml | 11.6 | 11.4 | 11.6 | 11.8 | 11.8 | 11.8 | 11.6 | 11.4 | 11.6 | 11.4 | 11.6 |
| 13 μgm/ml | 9.8 | 9.6 | 9.8 | 9.6 | 9.8 | 9.8 | 9.6 | 9.4 | 9.6 | 9.8 | 9.7 |
| 6.5 μgm/ml | 9.4 | 9.4 | 9.6 | 9.4 | 9.6 | 9.4 | 9.6 | 9.6 | 9.4 | 9.2 | 9.5 |
| Buffer | 9.6 | 10.2 | 10.0 | 9.8 | 10.0 | 10.2 | 10.0 | 10.2 | 10.4 | 9.6 | 10.0 |

TABLE 5

Summary - - - Mean Height of Tomato Plants after Treatment.

| Treatment | | Mean height of tomato plants (cm) | | |
|---|---|---|---|---|
| Day 0 | Day 1 | Day 15 | Day 21 | Day 27 |
| Harpin seed soak (1:15) | sowing | 5.7 | 7.7 | 10.5 |
| Harpin seed soak (1:30) | sowing | 7.0 | 8.6 | 11.6 |
| Harpin seed soak (1:60) | sowing | 5.9 | 6.9 | 9.7 |
| Harpin seed soak (1:120) | sowing | 5.4 | 6.7 | 9.5 |
| Buffer seed soak | sowing | 5.3 | 6.5 | 10.0 |

As shown in Tables 2–5, the treatment of tomato seeds with *Erwinia amylovora* hypersensitive response elicitor increased plant growth. A 1:30 dilution had the greatest effect—a 16% increase in seedling height.

Example 3

Effect of Treating Tomato Plants with *Erwinia amylovora* Hypersensitive Response Elicitor on Tomato Plant Height When Marglobe tomato plants were 4 weeks old, they were sprayed with 6 ml/plant of *Erwinia amylovora* harpin solution containing 13 μgm/ml (1:60) or 8.7 μgm/ml (1:90) of harpin or buffer (5 mM $KPO_4$) in a growth chamber at 28° C. The heights of tomato plants were measured 2 weeks after spraying harpin (6-week-old tomato plants) and 2 weeks plus 5 days after spraying. Ten uniform appearing plants per treatment were chosen randomly and measured. The seedlings were measured by ruler from the surface of soil to the top of plant.

Treatments:
1. Harpin (1:60) (13 μgm/ml).
2. Harpin (1:90) (8.7 μgm/ml).
3. Buffer (5 mM $KPO_4$, pH 6.8).

TABLE 6

Mean Height of Tomato Plants after Treatment With Harpin.

| Operation and Treatment | | | Mean height (cm) of tomato plants | |
|---|---|---|---|---|
| Day 0 | Day 14 | Day 28 | Day 42 | Day 47 |
| sowing | transplant | harpin 1:60 (13 μgm/ml) | 35.5 | 36.0 |
| sowing | transplant | harpin 1:90 (8.7 μgm/ml) | 35.7 | 36.5 |
| sowing | transplant | buffer | 32.5 | 33.0 |

As shown in Table 6, spraying tomato seedlings with *Erwinia amylovora* hypersensitive response elicitor can increase growth of tomato plants. Similar increases in growth were noted for the two doses of the hypersensitive response elicitor tested compared with the buffer-treated control.

Example 4

Effect of Treating Tomato Seeds with *Erwinia amylovora* Hypersensitive Response Elicitor on Tomato Plant Height Marglobe tomato seeds were submerged in *Erwinia amylovora* hypersensitive response elicitor solution ("harpin") (1:40, 1:80, 1:160, 1:320, and 1:640) or buffer in beakers on day 0 for 24 hours at 28° C. in the growth chamber. After soaking seeds in harpin or buffer, they were sown in germination pots with artificial soil on day 1. Ten uniform appearing plants per treatment were chosen randomly and measured. The seedlings were measured by ruler from the surface of soil to the top of plant.

Treatments:

1. Harpin (1:40) (20 $\mu$gm/ml).
2. Harpin (1:80) (10 $\mu$gm/ml).
3. Harpin (1:160) (5 $\mu$gm/ml).
4. Harpin (1:320) (2.5 $\mu$gm/ml).
5. Harpin (1:640) (1.25 $\mu$gm/ml).
6. Buffer (5 mM $KPO_4$, pH 6.8)

TABLE 7

Seedling Height (cm) 12 Days After Seed Treatment.

| Treat | Plants | 1 | 2 | 3 | 4 | 5 | 6 | 7 | 8 | 9 | 10 | Mean |
|---|---|---|---|---|---|---|---|---|---|---|---|---|
| 20 $\mu$gm/ml | 10 | 6.5 | 6.8 | 6.8 | 6.5 | 6.4 | 6.4 | 6.8 | 6.4 | 6.8 | 6.6 | 6.6 |
| 10 $\mu$gm/ml | 10 | 6.8 | 6.2 | 6.6 | 6.4 | 6.8 | 6.8 | 6.6 | 6.4 | 6.8 | 6.4 | 6.6 |
| 5 $\mu$gm/ml | 10 | 6.2 | 6.6 | 6.0 | 6.6 | 6.4 | 6.2 | 6.6 | 6.2 | 6.0 | 6.6 | 6.3 |
| 2.5 $\mu$gm/ml | 10 | 6.4 | 6.2 | 6.6 | 6.0 | 6.2 | 6.4 | 6.0 | 6.0 | 6.2 | 6.2 | 6.2 |
| 1.25 $\mu$gm/ml | 10 | 6.2 | 6.2 | 6.0 | 6.4 | 6.0 | 6.0 | 6.4 | 6.2 | 6.4 | 6.2 | 6.2 |
| Buffer | 10 | 5.8 | 6.0 | 6.2 | 6.2 | 5.8 | 5.8 | 6.0 | 6.2 | 6.0 | 6.0 | 6.0 |

TABLE 8

Seedling Height (cm) 14 Days After Seed Treatment.

| Treat | Plants | 1 | 2 | 3 | 4 | 5 | 6 | 7 | 8 | 9 | 10 | Mean |
|---|---|---|---|---|---|---|---|---|---|---|---|---|
| 20 $\mu$gm/ml | 10 | 7.8 | 7.8 | 8.2 | 8.0 | 8.2 | 8.4 | 7.8 | 8.4 | 7.6 | 7.8 | 8.0 |
| 10 $\mu$gm/ml | 10 | 8.6 | 8.8 | 8.4 | 9.2 | 8.4 | 8.6 | 7.8 | 7.8 | 8.4 | 8.4 | 8.4 |
| 5 $\mu$gm/ml | 10 | 9.8 | 9.2 | 9.8 | 9.6 | 9.2 | 9.4 | 8.6 | 9.2 | 9.0 | 8.6 | 9.2 |
| 2.5 $\mu$gm/ml | 10 | 8.8 | 8.6 | 8.6 | 8.4 | 7.8 | 8.6 | 8.4 | 9.0 | 8.0 | 7.8 | 8.4 |
| 1.25 $\mu$gm/ml | 10 | 8.4 | 7.8 | 8.4 | 8.0 | 8.6 | 8.4 | 8.0 | 8.2 | 8.4 | 8.2 | 8.2 |
| Buffer | 10 | 7.2 | 8.2 | 7.4 | 7.6 | 7.8 | 7.6 | 7.8 | 7.4 | 7.8 | 7.6 | 7.6 |

TABLE 9

Seedling Height (cm) 17 Days After Seed Treatment.

| Treat | Plants | 1 | 2 | 3 | 4 | 5 | 6 | 7 | 8 | 9 | 10 | Mean |
|---|---|---|---|---|---|---|---|---|---|---|---|---|
| 20 $\mu$gm/ml0 | 10 | 11.2 | 11.6 | 11.4 | 11.6 | 11.4 | 11.2 | 11.8 | 11.4 | 11.8 | 11.6 | 11.5 |
| 10 $\mu$gm/ml | 10 | 13.4 | 13.4 | 13.8 | 13.2 | 13.4 | 12.6 | 12.4 | 13.4 | 13.2 | 13.4 | 13.2 |
| 5 $\mu$gm/ml | 10 | 13.6 | 12.8 | 13.6 | 13.2 | 14.2 | 13.8 | 12.6 | 13.4 | 13.8 | 13.6 | 13.5 |
| 2.5 $\mu$gm/ml | 10 | 11.6 | 12.4 | 12.4 | 11.8 | 11.6 | 12.2 | 12.6 | 11.8 | 12.0 | 11.6 | 12.0 |
| 1.25 $\mu$gm/ml | 10 | 12.8 | 12.6 | 12.0 | 12.4 | 11.6 | 11.8 | 12.2 | 11.4 | 11.2 | 11.4 | 11.9 |
| Buffer | 10 | 10.0 | 10.4 | 10.6 | 10.6 | 10.4 | 10.4 | 10.8 | 10.2 | 10.4 | 10.0 | 10.4 |

TABLE 10

Summary - Mean Height of Tomato Plants After Treatment

| Operation and Treatment | Mean height of tomato plants (cm) | | | |
|---|---|---|---|---|
| Day 0 | Day 1 | Day 12 | Day 14 | Day 17 |
| Harpin seed soak (20 μgm/ml) | sowing | 6.6 | 8.0 | 11.5 |
| Harpin seed soak (10 μgm/ml) | sowing | 6.6 | 8.4 | 13.2 |
| Harpin seed soak (5 μgm/ml) | sowing | 6.3 | 9.2 | 13.5 |
| Harpin seed soak (2.5 μgm/ml) | sowing | 6.2 | 8.4 | 12.0 |

TABLE 10-continued

Summary - Mean Height of Tomato Plants After Treatment

| Operation and Treatment | Mean height of tomato plants (cm) | | | |
|---|---|---|---|---|
| Day 0 | Day 1 | Day 12 | Day 14 | Day 17 |
| Harpin seed soak (1.25 μgm/ml) | sowing | 6.2 | 8.2 | 11.9 |
| Buffer seed soak | sowing | 6.0 | 7.6 | 10.4 |

As shown in Tables 7–10, the treatment of tomato seeds with *Erwinia amylovora* hypersensitive response elicitor can increase growth of tomato plants. A 1:160 dilution (5 μg/ml harpin) had the greatest effect—seedling height was increased more than 20% over the buffer treated plants.

Example 5

Effect of Treating Tomato Seeds with *Erwinia amylovora* Hypersensitive Response Elicitor on Seed Germination Percentage Marglobe tomato seeds were submerged in 40 ml of *Erwinia amylovora* hypersensitive response elicitor ("harpin") solution (dilutions of CFEP from *E. coli* DH5 (pCPP2139) of 1:50 or 1:100 which contained, respectively, 8 $\mu$gm/ml and 4 $\mu$gm/ml of hypersensitive response elicitor) and buffer in beakers on day 0 for 24 hours at 28° C. in a growth chamber. After soaking, the seeds were sown in germination pots with artificial soil on day 1. This treatment was carried out on 20 seeds per pot and 4 pots per treatment.

Treatments:

1. Harpin (8 $\mu$gm/ml).
2. Harpin (8 $\mu$gm/ml).
3. Harpin (8 $\mu$gm/ml).
4. Harpin (8 $\mu$gm/ml).
5. Harpin (4 $\mu$gm/ml).
6. Harpin (4 $\mu$gm/ml).
7. Harpin (4 $\mu$gm/ml).
8. Harpin (4 $\mu$gm/ml).
9. Buffer (5 mM $KPO_4$, pH 6.8).
10. Buffer (5 mM $KPO_4$, pH 6.8).
11. Buffer (5 mM $KPO_4$, pH 6.8).
12. Buffer (5 mM $KPO_4$, pH 6.8).

TABLE 11

Number of Seedlings After Seed Treatment With Harpin

| Operation and Treatment | | Number of seeds germinated (out of a total of 20) | | | | | |
|---|---|---|---|---|---|---|---|
| Day 0 | Day 1 | Day 5 | Mean | Day 42 | Mean | Day 47 | Mean |
| Harpin (8 $\mu$gm/ml) | sowing | 11 | | 15 | | 19 | |
| Harpin (8 $\mu$gm/ml) | sowing | 13 | | 17 | | 20 | |
| Harpin (8 $\mu$gm/ml) | sowing | 10 | | 13 | | 16 | |
| Harpin (8 $\mu$gm/ml) | sowing | 9 | 10.8 | 15 | 15.0 | 16 | 17.8 |
| Harpin (4 $\mu$gm/ml) | sowing | 11 | | 17 | | 17 | |
| Harpin (4 $\mu$gm/ml) | sowing | 15 | | 17 | | 18 | |
| Harpin (4 $\mu$gm/ml) | sowing | 9 | | 12 | | 14 | |
| Harpin (4 $\mu$gm/ml) | sowing | 9 | 11.0 | 14 | 15.0 | 16 | 16.3 |
| Buffer | sowing | 11 | | 11 | | 14 | |
| Buffer | sowing | 9 | | 14 | | 15 | |
| Buffer | sowing | 10 | | 14 | | 14 | |
| Buffer | sowing | 10 | 10.0 | 12 | 12.8 | 14 | 14.3 |

As shown in Table 11, treatment of tomato seeds with *Erwinia amylovora* hypersensitive response elicitor can increase germination rate and level of tomato seeds. The higher dose used appeared to be more effective than buffer at the end of the experiment.

Example 6

Effect on Plant Growth of Treating Tomato Seeds with Proteins Prepared from *E. coli* Containing a Hypersensitive Response Elicitor Encoding Construct, pCPP2139, or Plasmid Vector pCPP50

Marglobe tomato seeds were submerged in *Erwinia amylovora* hypersensitive response elicitor ("harpin") (from *E. coli* DH5α(pCPP2139) (FIG. 1) or vector preparation (from DH5α(pCPP50) (FIG. 2) with added BSA protein as control. The control vector preparation contained, per ml, 33.6 $\mu$l of BSA (10 mg/ml) to provide about the same amount of protein as contained in the pCPP2139 preparation due to harpin. Dilutions of 1:50 (8.0 $\mu$g/ml), 1:100 (4.0 $\mu$g/ml), and 1:200 (2.0 $\mu$g/ml) were prepared in beakers on day 1, and seed was submerged for 24 hours at 28° C. in a controlled environment chamber. After soaking, seeds were sown in germination pots with artificial soil on day 2. Ten uniform appearing plants per treatment were chosen randomly and measured at three times after transplanting. The seedlings were measured by ruler from the surface of soil to the top of plant.

Treatments:

1. Harpin 1:50 (8.0 $\mu$g/ml)
2. Harpin 1:100 (4.0 $\mu$g/ml)
3. Harpin 1:200 (2.0 $\mu$g/ml)
4. Vector+BSA 1:50 (0 harpin)

5. Vector+BSA 1:100 (0 harpin)
6. Vector+BSA 1:200 (0 harpin)

TABLE 12

Seedling Height (cm) 18 Days After Seed Treatment

| Treat | Harpin | 1 | 2 | 3 | 4 | 5 | 6 | 7 | 8 | 9 | 10 | Mean |
|---|---|---|---|---|---|---|---|---|---|---|---|---|
| H1:50  | 8.0 | 3.6 | 5.0 | 4.8 | 5.0 | 4.2 | 5.2 | 5.8 | 4.6 | 4.0 | 4.8 | 4.7 |
| H1:100 | 4.0 | 4.6 | 5.8 | 6.2 | 6.0 | 5.6 | 6.8 | 6.0 | 4.8 | 5.6 | 6.2 | 5.8 |
| H1:200 | 2.0 | 4.0 | 5.8 | 5.8 | 4.6 | 5.4 | 5.0 | 5.8 | 4.6 | 4.6 | 5.8 | 5.1 |
| V1:50  | 0   | 3.8 | 5.0 | 4.6 | 5.4 | 5.6 | 4.6 | 5.0 | 5.2 | 4.6 | 4.8 | 4.9 |
| V1:100 | 0   | 4.4 | 5.2 | 4.6 | 4.4 | 5.4 | 4.8 | 5.0 | 4.6 | 4.4 | 5.2 | 4.8 |
| V1:200 | 0   | 4.2 | 4.8 | 5.4 | 4.6 | 5.0 | 4.8 | 4.8 | 5.4 | 4.6 | 5.0 | 4.9 |

TABLE 13

Seedling Height (cm) 22 Days After Seed Treatment.

| Treat | Harpin | 1 | 2 | 3 | 4 | 5 | 6 | 7 | 8 | 9 | 10 | Mean |
|---|---|---|---|---|---|---|---|---|---|---|---|---|
| H1:50  | 8.0 | 4.2 | 5.6 | 5.2 | 6.0 | 4.8 | 5.4 | 5.0 | 5.2 | 5.4 | 5.0 | 5.2 |
| H1:100 | 4.0 | 7.6 | 6.8 | 7.0 | 7.2 | 6.8 | 7.4 | 7.6 | 7.0 | 6.8 | 7.4 | 7.2 |
| H1:200 | 2.0 | 7.0 | 6.6 | 6.8 | 7.2 | 7.4 | 6.8 | 7.0 | 7.2 | 6.8 | 7.2 | 7.0 |
| V1:50  | 0   | 5.6 | 5.8 | 6.2 | 6.4 | 5.6 | 5.2 | 5.6 | 5.8 | 6.0 | 5.8 | 5.8 |
| V1:100 | 0   | 5.4 | 6.0 | 5.8 | 6.2 | 5.8 | 5.6 | 5.4 | 5.2 | 6.0 | 5.6 | 5.7 |
| V1:200 | 0   | 5.2 | 6.2 | 5.8 | 5.4 | 6.2 | 6.0 | 5.6 | 6.4 | 5.8 | 6.0 | 5.9 |

TABLE 14

Seedling Height (cm) 26 Days After Seed Treatment.

| Treat. | Harpin | 1 | 2 | 3 | 4 | 5 | 6 | 7 | 8 | 9 | 10 | Mean |
|---|---|---|---|---|---|---|---|---|---|---|---|---|
| H1:50  | 8.0 | 7.6  | 8.4  | 8.8  | 6.8  | 9.6  | 8.2  | 7.4  | 9.8  | 9.2  | 9.0  | 8.5  |
| H1:100 | 4.0 | 12.0 | 11.4 | 11.2 | 11.0 | 10.8 | 12.0 | 11.2 | 11.6 | 10.4 | 10.2 | 11.2 |
| H1:200 | 2.0 | 10.6 | 11.2 | 11.6 | 10.2 | 11.0 | 10.8 | 10.0 | 11.8 | 10.2 | 10.6 | 10.8 |
| V1:50  | 0   | 9.0  | 9.4  | 8.8  | 8.4  | 9.6  | 9.2  | 9.2  | 8.6  | 8.0  | 9.4  | 9.2  |
| V1:100 | 0   | 9.2  | 10.0 | 9.8  | 9.6  | 8.4  | 9.4  | 9.6  | 9.8  | 8.0  | 9.6  | 9.3  |
| V1:200 | 0   | 8.8  | 9.6  | 8.2  | 9.2  | 8.4  | 8.0  | 9.8  | 9.0  | 9.4  | 9.2  | 9.0  |

TABLE 15

Mean Height of Tomato Plants After Treatment

| Operation and Treatment | | Mean height of tomato plants (cm) | | |
|---|---|---|---|---|
| Day 1 | Day 2 | Day 18 | Day 22 | Day 26 |
| Harpin (1:50) (8.0 µgm/ml)  | sowing | 4.7 | 5.2 | 8.5  |
| Harpin (1:100) (4.0 µgm/ml) | sowing | 5.8 | 7.2 | 11.2 |
| Harpin (1:200) (2.0 µgm/ml) | sowing | 5.1 | 7.0 | 10.8 |
| Vector + BSA (1:50)  (0)    | sowing | 4.9 | 5.8 | 9.2  |
| Vector + BSA (1:100) (0)    | sowing | 4.8 | 5.7 | 9.3  |
| Vector + BSA (1:200) (0)    | sowing | 4.9 | 5.9 | 9.0  |

As shown in Tables 12–15, treatment with *E. coli* containing the gene encoding the *Erwinia amylovora* h TABLE 16-continued Seedling Height (cm) 11 Days After Seed Treatment

| Treat. | Harpin | Plants | 1 | 2 | 3 | 4 | 5 | 6 | 7 | 8 | 9 | 10 | Mean |
|---|---|---|---|---|---|---|---|---|---|---|---|---|---|
| V1:50 | 0 | 10 | 4.8 | 4.4 | 4.6 | 4.0 | 4.4 | 4.2 | 4.6 | 4.0 | 4.4 | 4.2 | 4.4 |
| V1:100 | 0 | 10 | 4.6 | 4.2 | 4.8 | 4.4 | 4.4 | 4.0 | 4.2 | 4.0 | 4.4 | 4.0 | 4.3 |

TABLE 17

Seedling Height (cm) 14 Days After Seed Treatment

| Treat. | Harpin | Plants | 1 | 2 | 3 | 4 | 5 | 6 | 7 | 8 | 9 | 10 | Mean |
|---|---|---|---|---|---|---|---|---|---|---|---|---|---|
| H1:25 | 16 µgm/ml | 10 | 7.6 | 7.6 | 7.2 | 7.4 | 7.8 | 7.8 | 7.6 | 7.0 | 7.4 | 7.0 | 7.4 |
| H1:50 | 8 µgm/ml | 10 | 8.5 | 8.2 | 8.4 | 7.6 | 7.8 | 8.4 | 8.6 | 9.0 | 7.6 | 8.2 | 8.2 |
| H1:100 | 4 µgm/ml | 10 | 7.2 | 8.4 | 8.2 | 7.4 | 8.0 | 7.6 | 7.6 | 8.0 | 8.6 | 7.6 | 7.9 |
| V1:25 | 0 | 10 | 6.8 | 6.4 | 7.8 | 6.6 | 6.6 | 6.8 | 7.4 | 6.0 | 6.4 | 6.4 | 6.7 |
| V1:50 | 0 | 10 | 6.6 | 5.8 | 6.4 | 7.6 | 7.4 | 7.2 | 6.8 | 6.6 | 6.4 | 5.8 | 6.7 |
| V1:100 | 0 | 10 | 6.2 | 6.0 | 6.8 | 6.6 | 6.4 | 5.8 | 6.6 | 7.0 | 5.8 | 6.4 | 6.4 |

TABLE 18

Mean Height of Tomato Plants After Treatment

| Operation and Treatment | | Mean height of tomato plants (cm) | |
|---|---|---|---|
| Day 1 | Day 2 | Day 11 | Day 14 |
| Harpin seed soak (16 µgm/ml) | sowing | 4.5 | 7.4 |
| Harpin seed soak (8 µgm/ml) | sowing | 5.5 | 8.2 |
| Harpin seed soak (4 µgm/ml) | sowing | 5.1 | 7.9 |
| Vector seed soak (16 µgm/ml) | sowing | 4.5 | 6.7 |
| Vector seed soak (8 µgm/ml) | sowing | 4.4 | 6.7 |
| Vector seed soak (4 µgm/ml) | sowing | 4.3 | 6.4 |

As shown in Tables 16–18, treatment with *Erwinia amylovora* hypersensitive response elicitor can increase growth of tomato plants. A 1:50 dilution (8 µg/ml hypersensitive response elicitor) had the greatest effect with seedling height being increased by about 20% over the control.

Example 8

Effect of Cell-Free *Erwinia amylovora* Hypersensitive Response Elicitor on Growth of Potato Three-week-old potato plants, variety Norchip, were grown from tuber pieces in individual containers. The foliage of each plant was sprayed with a solution containing *Erwinia amylovora* hypersensitive response elicitor ("harpin"), or a control solution containing proteins of *E. coli* and those of the vector pCPP50 ("vector"), diluted 1:50, 1:100, and 1:200. On day 20, 12 uniform appearing plants were chosen randomly for each of the following treatments. One plant from each treatment was maintained at 16° C., in a growth chamber, while two plants from each treatment were maintained on a greenhouse bench at 18–25° C. Twenty-five days after treatment, the shoots (stems) on all plants were measured individually.

Treatments:

1. Harpin 1:50 16 μgm/ml
2. Harpin 1:100 8 μgm/ml
3. Harpin 1:200 4 μgm/ml
4. Vector 1:50 0 harpin
5. Vector 1:100 0 harpin
6. Vector 1:200 0 harpin

TABLE 19

Length of Potato Stems of Plants at 16° C.

| Treatment | Length of potato stems (cm) stem on day 45 | | | | | | |
|---|---|---|---|---|---|---|---|
| on day 20 | stem 1 | stem 2 | stem 3 | stem 4 | stem 5 | stem 6 | Plant Mean |
| Harpin 1:50 | 43.0 | 39.5 | 42.5 | 34.0 | 38.0 | 39.5 | 39.4 |
| Harpin 1:100 | 42.0 | 38.5 | (2 branch) | | | | 40.3 |
| Harpin 1:200 | 35.5 | 30.5 | 31.5 | (3 branch) | | | 32.5 |
| Vector 1:50 | 34.0 | 32.0 | 31.5 | 28.0 | 27.5 | (5 branch) | 30.6 |
| Vector 1:100 | 30.0 | 33.5 | 33.0 | 30.0 | 28.0 | 33.0 | 31.3 |
| Vector 1:200 | 33.5 | 31.5 | 32.5 | (3 branch) | | | 32.5 |

TABLE 20

Length of Potato Stems of Plants on a Greenhouse Bench

| Treatment on day 20 | Length of potato stems (cm) on day 45 | | | | | | | |
|---|---|---|---|---|---|---|---|---|
| | stem 1 | stem 2 | stem 3 | stem 4 | stem 5 | stem 6 | Plant | Treat. Mean |
| Harpin 1:50 | 65.5 | 58.5 | 57.5 | 62.5 | 68.5 | (5 branch) | 62.5 | |
| Harpin 1:50 | 62.5 | 67.0 | 65.0 | 69.0 | (4 branch) | | 65.9 | 64.2 |
| Harpin 1:100 | 70.5 | 73.5 | 74.0 | 80.5 | (4 branch) | | 74.6 | |
| Harpin 1:100 | 83.0 | 80.5 | 76.5 | 76.0 | 81.5 | (5 branch) | 79.5 | 77.1 |
| Harpin 1:200 | 56.5 | 59.5 | 50.5 | 53.0 | 55.5 | 48.0 | 53.9 | |
| Harpin 1:200 | 57.0 | 59.5 | 69.5 | (3 branch) | | | 62.0 | 58.0 |
| Vector 1:50 | 53.0 | 62.0 | 59.5 | 62.5 | (4 branch) | | 59.3 | |
| Vector 1:50 | 52.0 | 46.0 | 61.5 | 56.5 | 61.5 | 57.0 | 55.8 | 57.6 |
| Vector 1:100 | 62.0 | 51.5 | 66.0 | 67.5 | 62.0 | 63.0 | 62.0 | |
| Vector 1:100 | 61.5 | 62.5 | 59.0 | 65.5 | 63.0 | 63.5 | 62.5 | 62.3 |
| Vector 1:200 | 62.0 | 66.0 | (2 branch) | | | | 64.0 | |
| Vector 1:200 | 61.0 | 60.0 | 63.5 | (3 branch) | | | 61.5 | 62.8 |

As shown in Tables 19 and 20, treatment of potato plants with *Erwinia amylovora* hypersensitive response elicitor enhanced shoot (stem) growth. Thus, overall growth, as judged by both the number and mean lengths of stems, were greater in the harpin-treated plants in both the greenhouse and growth chamber-grown plants. The potato plants treated with the medium dose of harpin (8 μgm/ml) seemed enhanced in their stem growth more than those treated with either higher or lower doses. Treatment with the medium dose of harpin resulted in greater growth under both growing conditions.

Example 9
Effect of Spraying Tomatoes with a Cell-Free Elicitor Preparation Containing the *Erwinia amylovora* Harpin le;2qMarglobe tomato plants were sprayed with harpin preparation (from *E. coli* DH5α(pCPP2139)) or vector preparation (from *E. coli* DH5α(pCPP50)) with added BSA protein as control 8 days after transplanting. The control vector preparation contained, per ml, 33.6 μl of BSA (10 mg/ml) to provide about the same amount of protein as contained in the pCPP2139 preparation due to harpin. Dilutions of 1:50 (8.0 μg/ml), 1:100 (4.0 μg/ml), and 1:200 (2.0 μg/ml) were prepared and sprayed on the plants to runoff with an electricity-powered atomizer. Fifteen uniform appearing plants per treatment were chosen randomly and assigned to treatment. The plants were maintained at 28° C. in a controlled environment chamber before and after treatment.

Overall heights were measured several times after treatment from the surface of soil to the top of the plant. The tops of the tomato plants were weighed immediately after cutting the stems near the surface of the soil.

Treatments: (Dilutions and Harpin Content)
1. Harpin 1:50 (8.0 μg/ml)
2. Harpin 1:100 (4.0 μg/ml)
3. Harpin 1:200 (2.0 μg/ml)
4. Vector+BSA 1:50 (0 harpin)
5. Vector+BSA 1:100 (0 harpin)
6. Vector+BSA 1:200 (0 harpin)

TABLE 21

Tomato plant height (cm) 1 day after spray treatment

| Treat | 1 | 2 | 3 | 4 | 5 | 6 | 7 | 8 | 9 | 10 | 11 | 12 | 13 | 14 | 15 | Mean |
|---|---|---|---|---|---|---|---|---|---|---|---|---|---|---|---|---|
| H 50 | 5.4 | 5.0 | 5.6 | 5.0 | 5.2 | 4.8 | 5.0 | 5.2 | 5.4 | 5.0 | 5.6 | 4.8 | 4.6 | 5.0 | 5.8 | 5.16 |
| H 100 | 5.0 | 5.2 | 5.0 | 5.4 | 5.4 | 5.0 | 5.2 | 4.8 | 5.6 | 5.2 | 5.4 | 5.0 | 4.8 | 5.0 | 5.2 | 5.15 |
| H 200 | 5.0 | 4.6 | 5.4 | 4.6 | 5.0 | 5.2 | 5.4 | 4.8 | 5.0 | 5.2 | 5.4 | 5.2 | 5.0 | 5.2 | 5.0 | 5.13 |
| V 50 | 5.2 | 4.6 | 4.8 | 5.0 | 5.6 | 4.8 | 5.0 | 5.2 | 5.6 | 5.4 | 5.2 | 5.8 | 5.0 | 4.8 | 5.2 | 5.15 |
| V 100 | 5.2 | 4.8 | 5.2 | 5.0 | 5.6 | 4.8 | 5.4 | 5.2 | 5.0 | 4.8 | 5.0 | 4.8 | 5.6 | 5.2 | 5.4 | 5.13 |
| V 200 | 5.2 | 5.4 | 5.0 | 5.4 | 5.2 | 5.4 | 5.0 | 5.2 | 5.4 | 5.2 | 4.6 | 4.8 | 5.2 | 5.0 | 5.4 | 5.16 |

TABLE 22

Tomato plant height (cm) 15 days after spray treatment

| Treat | 1 | 2 | 3 | 4 | 5 | 6 | 7 | 8 | 9 | 10 | 11 | 12 | 13 | 14 | 15 | Mean |
|---|---|---|---|---|---|---|---|---|---|---|---|---|---|---|---|---|
| H 50 | 22.0 | 21.0 | 22.0 | 21.5 | 23.0 | 22.0 | 23.5 | 25.0 | 22.0 | 20.5 | 21.0 | 23.5 | 22.0 | 22.5 | 21.0 | 22.2 |
| H 100 | 26.0 | 26.5 | 27.0 | 29.0 | 27.5 | 26.0 | 28.0 | 29.0 | 28.5 | 26.0 | 27.5 | 28.0 | 28.0 | 29.0 | 26.0 | 27.5 |
| H 200 | 24.5 | 26.0 | 25.0 | 26.0 | 26.5 | 27.5 | 28.5 | 28.0 | 26.0 | 24.0 | 26.5 | 24.5 | 26.0 | 24.0 | 27.5 | 26.0 |
| V 50 | 23.5 | 21.5 | 20.5 | 22.5 | 20.5 | 21.0 | 22.0 | 23.5 | 22.0 | 20.5 | 22.0 | 21.0 | 20.5 | 22.5 | 21.5 | 21.7 |
| V 100 | 22.5 | 21.0 | 20.5 | 23.0 | 22.0 | 20.0 | 20.5 | 20.0 | 21.0 | 22.0 | 23.0 | 20.0 | 22.0 | 21.0 | 22.5 | 21.4 |
| V 200 | 21.5 | 20.5 | 23.5 | 20.5 | 22.0 | 22.0 | 22.5 | 20.0 | 22.0 | 23.5 | 23.5 | 22.0 | 20.0 | 23.0 | 21.0 | 21.8 |

TABLE 23

Tomato plant height (cm) 21 days after spray treatment

| Treat | 1 | 2 | 3 | 4 | 5 | 6 | 7 | 8 | 9 | 10 | 11 | 12 | 13 | 14 | 15 | Mean |
|---|---|---|---|---|---|---|---|---|---|---|---|---|---|---|---|---|
| H 50 | 28.5 | 28.0 | 27.5 | 26.0 | 27.0 | 28.5 | 28.5 | 29.0 | 30.0 | 28.5 | 29.0 | 27.0 | 28.5 | 28.0 | 27.0 | 28.1 |
| H 100 | 37.0 | 38.0 | 37.5 | 39.0 | 37.0 | 38.5 | 36.0 | 38.0 | 37.0 | 38.5 | 37.0 | 36.0 | 37.0 | 37.0 | 38.5 | 37.5 |
| H 200 | 34.5 | 34.0 | 36.0 | 33.5 | 32.0 | 34.5 | 32.5 | 34.0 | 32.0 | 36.5 | 30.5 | 32.0 | 30.0 | 32.5 | 34.0 | 33.2 |
| V 50 | 30.0 | 28.0 | 28.0 | 28.5 | 30.0 | 27.0 | 26.5 | 28.0 | 29.5 | 28.5 | 26.5 | 28.5 | 27.0 | 29.5 | 28.5 | 28.3 |
| V 100 | 28.0 | 27.5 | 30.0 | 29.5 | 28.5 | 29.0 | 30.0 | 26.5 | 27.5 | 28.0 | 30.0 | 29.0 | 28.5 | 28.0 | 29.5 | 28.6 |
| V 200 | 28.5 | 30.5 | 27.0 | 29.0 | 28.5 | 27.5 | 29.0 | 30.0 | 28.0 | 28.5 | 29.0 | 30.5 | 27.5 | 28.5 | 28.0 | 28.7 |

TABLE 24

Mean Height of Tomato Plants After Spraying

| Treatment (Dil. & harpin) | | Mean height of tomato plants (cm) Days After Treatment | | |
|---|---|---|---|---|
| | | Day 1 | Day 11 | Day 14 |
| Harpin 1:50 | (8.0 μg/ml) | 5.15 | 22.2 | 28.1 |
| Harpin 1:100 | (4.0 μg/ml) | 5.15 | 27.5 | 37.5 |
| Harpin 1:200 | (2.0 μg/ml) | 5.13 | 26.0 | 33.2 |
| Vector + BSA 1:50 | (0) | 5.15 | 21.7 | 28.5 |
| Vector + BSA 1:100 | (0) | 5.13 | 21.4 | 28.6 |
| Vector + BSA 1:200 | (0) | 5.16 | 21.8 | 28.7 |

TABLE 25

Fresh Weight of Tomato Plants (g/plant) 21 Days After Spray Treatment

| Treat | 1 | 2 | 3 | 4 | 5 | 6 | 7 | 8 | 9 | 10 | 11 | 12 | 13 | 14 | 15 | Mean |
|---|---|---|---|---|---|---|---|---|---|---|---|---|---|---|---|---|
| H 50 | 65.4 | 60.3 | 58.9 | 73.2 | 63.8 | 70.1 | 58.4 | 60.1 | 62.7 | 55.6 | 58.3 | 68.9 | 58.2 | 64.2 | 56.4 | 62.3 |
| H 100 | 84.3 | 68.8 | 74.6 | 66.7 | 78.5 | 58.9 | 76.4 | 78.6 | 84.8 | 78.4 | 86.4 | 66.5 | 76.5 | 82.4 | 80.5 | 76.2 |
| H 200 | 80.1 | 76.5 | 68.4 | 79.5 | 64.8 | 79.6 | 76.4 | 80.2 | 66.8 | 72.5 | 78.8 | 72.3 | 62.8 | 76.4 | 73.2 | 73.9 |
| V 50 | 64.0 | 56.8 | 69.4 | 72.3 | 56.7 | 66.8 | 71.2 | 62.3 | 61.0 | 62.5 | 63.4 | 58.3 | 72.1 | 67.8 | 67.0 | 64.7 |
| V 100 | 62.8 | 58.4 | 70.2 | 64.2 | 58.1 | 72.7 | 68.4 | 53.6 | 67.5 | 66.3 | 59.3 | 68.2 | 71.2 | 65.2 | 59.2 | 64.4 |
| V 200 | 64.2 | 59.6 | 70.2 | 66.6 | 64.3 | 60.4 | 60.8 | 56.7 | 71.8 | 60.6 | 63.6 | 58.9 | 68.3 | 57.2 | 60.0 | 62.9 |

A single spray of tomato seedlings with harpin, in general, resulted in greater subsequent growth than spray treatment with the control (vector) preparation, which had been supplemented with BSA protein. Enhanced growth in the harpin-treated plants was seen in both plant height and fresh weight measurements. Of the three concentrations tested, the two lower ones resulted in more plant growth (based on either measure) than the higher dose (8.0 μg/ml). There was little difference in the growth of plants treated with the two lower (2 and 4 μg/ml) concentrations. Components of the lysed cell preparation from the strain *E. coli* DH5α (pCPP50), which harbors the vector of the hrpN gene in *E. coli* strain DH5α(pCPP2139), do not have the same growth-promoting effect as the harpin-containing preparation, even though it is supplemented with BSA protein to the same extent as the DH5α(pCPP2139) preparation, which contains large amounts of harpin protein. Thus, this experiment demonstrates that harpin is responsible for enhanced plant growth.

Example 10
Early Coloration and Early Ripening of Raspberry Fruits

A field trial was conducted to evaluate the effect of hypersensitive response elicitor ("harpin") treatment on yield and ripening parameters of raspberry cv. Canby. Established plants were treated with harpin at 2.5 mg/100 square feet in plots 40 feet long×3 feet wide (1 plant wide), untreated ("Check"), or treated with the industry standard chemical Ronilan at recommended rates ("Ronilan"). Treatments were replicated four times and arranged by rep in an experimental field site. Treatments were made beginning at 5–10% bloom followed by two applications at 7–10 day intervals. The first two harvests were used to evaluate disease control and fruit yield data was collected from the last two harvests. Observations indicated harpin-treated fruits were larger and exhibited more redness than untreated fruits, indicating ripening was accelerated by 1–2 weeks. The number of ripe fruits per cluster bearing a minimum of ten fruits was determined at this time and is summarized in Table 26. Harpin treated plots had more ripe fruits per 10-berry cluster than either the check or Ronilan treatments.

Combined yields from the last two harvests indicated increased yield in harpin and Ronilan treated plots over the untreated control (Table 27).

TABLE 26

Number of Ripe Raspberry Fruits Per Clusters With Ten Berries or More on June 20, 1996.

| Treatment | Ripe fruit/10 berry clusters | % of Control |
|---|---|---|
| Check | 2.75 | 100.0 |
| Ronilan | 2.75 | 100.0 |
| Harpin | 7.25 | 263.6 |

TABLE 27

Mean Raspberry Fruit Yield by Weight (lbs.) Combined in Last Two Harvest.

| Treatment | Total Yield | % of Control |
|---|---|---|
| Check | 32.5 | 100.0 |
| Ronilan | 37.5 | 115.4 |
| Harpin | 39.5 | 121.5 |

Example 11
Growth Enhancement for Snap Beans

Snap beans of the variety Bush Blue Lake were treated by various methods, planted in 25-cm-d plastic pots filled with commercial potting mix, and placed in an open greenhouse for the evaluation of growth parameters. Treatments included untreated bean seeds ("Check"), seeds treated with a slurry of 1.5% methyl cellulose prepared with water as diluent ("M/C"), seeds treated with 1.5% methyl cellulose followed by a foliar application of hypersensitive response elicitor ("harpin") at 0.125 mg/ml ("M/C+H"), and seeds treated with 1.5% methyl cellulose plus harpin spray dried at 5.0 µg harpin per 50 seeds followed by a foliar application of harpin at 0.125 mg/ml ("M/C−SD+H"). Seeds were sown on day 0, planted 3 per pot, and thinned to 1 plant per pot upon germination. Treatments were replicated 10 times and randomized by rep in an open greenhouse. Bean pods were harvested after 64 days, and fresh weights of bean pods of marketable size (>10 cm×5 cm in size) were collected as yield. Data were analyzed by analysis of variance with Fisher's LSD used to separate treatment means.

TABLE 28

Effect of *Erwinia amylovora* Harpin Treatment by Various Methods on Yield of Market Sized Snap Bean Pods

| Treatment | Marketable Yield, q[1] | % of Untreated (Check) |
| --- | --- | --- |
| M/C − SD + H | 70.6 a | 452 |
| M/C − H | 58.5 ab | 375 |
| M/C | 46.3 bc | 297 |
| M/C + H | 42.3 bc | 271 |
| M/C − SD | 40.0 cd | 256 |
| Check | 15.6 e | 100 |

[1]Marketable yield included all bean pods 10 cm × 0.5 cm or larger. Means followed by the same letter are not significantly different at P = 0.05 according to Fisher's LSD.

As shown in Table 28, the application of *Erwinia amylovora* harpin by various methods of application resulted in an increase in the yield of marketable size snap bean pods. Treatment with methyl cellulose alone also results in an increase in bean yield but was substantially increased when combined with harpin as seed (spray dried) and foliar treatments.

Example 12

Yield Increase in Cucumbers from Foliar Application of HP-1000™ to Cucumbers.

Cucumber seedlings and transplants were treated with foliar sprays of HP-1000™ hypersensitive response elicitor protein (hereinafter "HP-1000™") (EDEN Bioscience, Bothell, Wash.) (*Erwinia amylovora* hypersensitive response elicitor formulation) at rates of 15, 30, or 60 μg/ml active ingredient (a.i.). The first spray was applied when the first true leaves were fully expanded. The second application was made 10 days after the first spray. All sprays were applied using a back-pack sprayer, and an untreated control (UTC) was also included in the trial. Three days after the second application of HP-1000™, ten plants from each treatment were transplanted into randomized field plots replicated three times. This yielded a total of thirty plants per treatment. Seven days after transplanting, a third foliar spray of HP-1000™ was applied. Although severe drought followed resulting in significant water stress, a total of six harvests were made following a standard commercial harvesting pattern. The total weight of fruit harvested from each treatment is presented in Table 29. Results indicate that plants treated with HP-1000™ at rates of 15 and 30 μg/ml yielded significantly more fruit than the UTC. Plants treated with HP-1000™ yielded a moderate yield increase. These results indicated that HP-1000™ treated plants were significantly more tolerant to drought stress conditions than untreated plants.

TABLE 29

Increase yield of cucumbers after treatment with HP-1000 ™

| Treatment | Rate[1] | Yield,[2] lbs./10 plants | % above UTC |
|---|---|---|---|
| UTC | - - - | 9.7 a | - - - |
| HP-1000 ™ | 15 μg/ml | 25.4 b | 161.4 |
| HP-1000 ™ | 30 μg/ml | 32.6 c | 236.4 |
| HP-1000 ™ | 60 μg/ml | 11.2 a | 15.9 |

[1]Active ingredient (a.i.).
[2]Means followed by different letters are significantly different according to Duncan's MRT, P = 0.05.

Example 13

Yield Increase in Cotton from Treatment with HP-1000™

Cotton was planted in four, 12×20 foot replicate field plots in a randomized complete block (RCB) field trial. Plants were treated with HP-1000™ (EDEN Bioscience) (*Erwinia amylovora* hypersensitive response elicitor formulation), HP-1000™+Pix® (Pix® (BASF Corp., Mount Olive, N.J.) is a growth regulator applied to keep cotton plants compact in height) or Early Harvest® (Griffen Corp., Valdosta, Ga.) (a competitive growth enhancing agent). An untreated control (UTC) was also included in the trial. Using a back-pack sprayer, foliar applications were made of all treatments at three crop growth stages; first true leaves, pre-bloom, and early bloom. All fertilizers and weed control products were applied according to conventional farming practices for all treatments. The number of cotton bolls per plant ten weeks before harvest was significantly higher for the HP-1000™ treated plants compared to other treatments. By harvest, HP-1000™ treatment was shown to have a significantly increased lint yield (43%) compared to UTC (Table 30). When HP-1000™ was combined with Pix®, lint yield was increased 20% over UTC. Since Pix® is commonly applied to large acreages of cotton, this result indicates that HP-1000™ may be successfully tank-mixed with Pix®. Application of the competitive growth enhancing agent, Early Harvest® only produced a 9% increase in lint yield vs. UTC.

TABLE 30

Increased lint yield from cotton after treatment with HP-1000 ™, HP-1000 ™ + Pix ®, or Early Harvest ®

| Treatment | Rate[1] | Lint Yield (lbs./ac) | % above UTC |
|---|---|---|---|
| UTC | — | 942.1 | — |
| Early Harvest ® | 2 oz./ac. | 1,077.4* | 14.3 |
| HP-1000 ™ + Pix ® | 40 μg/ml + 8 oz./ac. | 1,133.1* | 20.4 |
| HP-1000 ™ | 40 μg/ml | 1,350.0* | 43.3 |
| (*significant at P = 0.05) | | lsd = 122.4 | |

[1]Rates for HP-1000 ™ are for active ingredient (a.i.); rates for Early Harvest ® and Pix ® are formulated product.

Example 14

Yield Increase of Chinese Egg Plant from Treatment with HP-1000™

Nursery grown Chinese egg plant seedlings were sprayed once with HP-1000™ at (EDEN Bioscience) (*Erwinia amylovora* hypersensitive response elicitor formulation) 15, 30, or 60 μg/ml (a.i.), then transplanted into field plots replicated three times for each treatment. Two weeks after transplanting, a second application of HP-1000™ was made. A third and final application of HP-1000™ was applied approximately two weeks after the second spray. All sprays were applied using a back-pack sprayer; an untreated control (UTC) was also included in the trial. As the season progressed, a total of eight harvests from each treatment were made. Data from these harvests indicate that treatment with HP-1000™ resulted in greater yield of fruit per plant.

TABLE 31

Increased yield for Chinese egg plant after Treatment with HP-1000 ™.

| Treatment | Rate (a.i.) | Yield (lbs./plant) | % above UTC |
|---|---|---|---|
| UTC | — | 1.45 | — |
| HP-1000 ™ | 15 µg/ml | 2.03 | 40.0 |
| HP-1000 ™ | 30 µg/ml | 1.90 | 31.0 |
| HP-1000 ™ | 60 µg/ml | 1.95 | 34.5 |

Example 15
Yield Increase of Rice from Treatment with HP-1000™

Rice seedlings were transplanted into field plots replicated three times, then treated with foliar sprays of HP-1000™ (EDEN Bioscience) (*Erwinia amylovora* hypersensitive response elicitor formulation) at three different rates using a back-pack sprayer. An untreated control (UTC) was also included in the trial. The first application of HP-1000™ was made one week after transplanting, the second three weeks after the first. A third and final spray was made just before rice grains began to fill the heads. Results at harvest demonstrated that foliar applications of HP-1000™ at both 30 and 60 μg/ml significantly increased yield by 47 and 56%, respectively (Table 32).

TABLE 32

Increase yield of rice after foliar treatment with HP-1000 ™.

| Treatment | Rate (a.i.) | Yield[1] (lbs./ac.) | % above UTC |
|---|---|---|---|
| UTC | — | 3,853 a | — |
| HP-1000 ™ | 15 μg/ml | 5,265 ab | 35.9 |
| HP-1000 ™ | 30 μg/ml | 5,710 b | 47.3 |
| HP-1000 ™ | 60 μg/ml | 6,043 b | 56.1 |

[1]Means followed by different letters are significantly different according to Duncan's MRT, P = 0.05.

Example 16

Yield Increase of Soybeans from Treatment with HP-1000™

Soybeans were planted into randomized field plots replicated three times for each treatment. A back-pack sprayer was used to apply foliar sprays of HP-1000™ (EDEN Bioscience) (*Erwinia amylovora* hypersensitive response elicitor formulation) and an untreated control (UTC) was also included in the trial. Three rates of HP-1000™ were applied beginning at four true leaves when plants were approximately eight inches tall. A second spray of HP-1000™ was applied ten days after the first spray and a third spray ten days after the second. Plant height measured ten days after the first spray treatment indicated that application of HP-1000™ resulted in significant growth enhancement (Table 33). In addition, plants treated with HP-1000™ at the rate of 60 μg/ml began to flower five days earlier than the other treatments. Approximately ten days after application of the third spray, the number of soybean pods per plant was counted from ten randomly selected plants per replication. These results indicated that the growth enhancement from treatment with HP-1000™ resulted in significantly greater yield (Table 34).

TABLE 33

Increased plant height of soybeans after foliar treatment with HP-1000 ™.

| Treatment | Rate (a.i.) | Plant Ht.[1] (in.) | % above UTC |
|---|---|---|---|
| UTC | — | 12.2 a | — |
| HP-1000 ™ | 15 μg/ml | 13.2 b | 8.3 |
| HP-1000 ™ | 30 μg/ml | 14.1 c | 16.2 |
| HP-1000 ™ | 60 μg/ml | 14.3 c | 17.3 |

[1]Means followed by different letters are significantly different according to Duncan's MRT, P = 0.05.

TABLE 34

Increased pod set of soybeans after foliar treatment with HP-1000 ™.

| Treatment | Rate (a.i.) | No. Pods/ plant[1] | % above UTC |
|---|---|---|---|
| UTC | — | 41.1 a | — |
| HP-1000 ™ | 15 μg/ml | 45.4 ab | 10.4 |
| HP-1000 ™ | 30 μg/ml | 47.4 b | 15.4 |
| HP-1000 ™ | 60 μg/ml | 48.4 b | 17.7 |

[1]Means followed by different letters are significantly different according to Duncan's MRT, P = 0.05.

Example 17

Yield Increase of Strawberries from Treatment with HP-1000™

Two field trials with HP-1000™ (EDEN Bioscience) (*Erwinia amylovora* hypersensitive response elicitor formulation) were conducted on two strawberry varieties, Camarosa and Selva. For each variety, a randomized complete block (RCB) design was established having four replicate plots (5.33×10 feet) per treatment in a commercially producing strawberry field. Within each plot, strawberry plants were planted in a double row layout. An untreated control (UTC) was also included in the trial. Before applications began, all plants were picked clean of any flowers and berries. Sprays of HP-1000™ at the rate of 40 μg/ml were applied as six weekly using a back-pack sprayer. Just prior to application of each spray, all ripe fruit from each treatment was harvested, weighed, and graded according to commercial standards. Within three weeks of the first application of HP-1000™ to Selva strawberry plants, growth enhancement was discernible as visibly greater above-ground biomass and a more vigorous, greener and healthier appearance. After six harvests (i.e. the scheduled life-span for these plants), all yield data were summed and analyzed. For the Camarosa variety, yield of marketable fruit from HP-1000™ treated plants was significantly increased (27%) over the UTC when averaged over the last four pickings (Table 35). Significant differences between treatments were not apparent for this variety for the first two pickings. The Selva variety was more responsive to the growth enhancing effects from treatment with HP-1000™; Selva strawberry plants yielded a statistically significant 64% more marketable fruit vs. the UTC when averaged over six pickings (Table 35).

TABLE 35

Increased yield of strawberries after foliar treatment with HP-1000 ™.

| Treatment | Rate (a.i.) | Yield[1] (lbs./rep.) | % above UTC |
|---|---|---|---|
| Variety: Camarosa | | | |
| UTC | — | 1.71 a | — |
| HP-1000 ™ | 40 µg/ml | 2.17 b | 27 |
| Variety: Selva | | | |
| UTC | — | 0.88 a | — |
| HP-1000 ™ | 40 µg/ml | 1.44 b | 64 |

[1]Means followed by different letters are significantly different according to Duncan's MRT, P = 0.05.

Example 18
Earlier Maturity and Increased Yield of Tomatoes from Treatment with HP-1000™

Fresh market tomatoes (var. Solar Set) were grown in plots (2×30 feet) replicated 5 times in a randomized complete block (RCB) field trial within a commercial tomato production field. Treatments included HP-1000™ (EDEN Bioscience) (*Erwinia amylovora* hypersensitive response elicitor formulation), an experimental competitive product (Actigard™ (Novartis, Greensboro, N.C.)) and a chemical standard (Kocide® (Griffen Corp., Valdosta, Ga.))+Maeb® (DuPont Agricultural Products, Wilmington, Del.)) for disease control. The initial application of HP-1000™ was made as a 50 ml drench (of 30 µg/ml a.i.) poured directly over the seedling immediately after transplanting. Thereafter, eleven weekly foliar sprays were applied using a back-pack sprayer. The first harvest from all treatments was made approximately six weeks after transplanting and only fully red, ripe tomatoes were harvested from each treatment. Results indicated that HP-1000™ treated plants had a significantly greater amount of tomatoes ready for the first harvest (Table 36). The tomatoes harvested from the HP-1000™ treated plants were estimated to be 10–14 days ahead other treatments.

TABLE 36

Increased yield of tomatoes at first harvest after foliar treatment with HP-1000 ™.

| Treatment | Rate (a.i.)[1] | Yield[2] (lbs./rep.) | % above UTC |
|---|---|---|---|
| UTC | — | 0.61 a | — |
| HP-1000 ™ | 30 µg/ml | 2.87 b | 375 |
| Actigard ™ | 14 g/ac | 0.45 a | −25.1 |
| Kocide ® + Maneb ® | 2 lbs. ac. 1 lb./ac. | 0.31 a | −49.1 |

[1]Rates for Kocide ® and Maneb ® are for formulated product.
[2]Means followed by different letters are significantly different according to Duncan's MRT, P = 0.05.

Example 19
Earlier Flowering and Growth Enhancement of Strawberries from Treatment with HP-1000™ when Planted in Non-fumigated Soil Strawberry plants ("plugs" and "bare-root"), cv. Commander were transplanted into plots (2×30 feet) replicated 5 times in a randomized complete block field trial. Approximately sixty individual plants were transplanted into each replicate. Treatments applied in this field trial are listed below:

| Treatment | Application method |
|---|---|
| HP-1000 ™ (plug plants) | 50-ml drench solution of HP-1000 ™ (EDEN Bioscience) (*Erwinia amylovora* hypersensitive response elicitor formulation) at 40 µg/ml (a.i.) poured directly over the individual plants immediately after transplanting into non-fumigated soil[1], followed by foliar applications of HP-1000 ™ at 40 µg/ml every 14 days. |
| HP-1000 ™ 40 (bare-root plants) | root soak in solution of HP-1000 ™ at µg/ml (a.i.) for 1 hour, immediately before transplanting into non-fumigated soil,[1] followed by foliar applications of HP-1000 ™ at 40 µg/ml every 14 days. |
| methyl bromide/ chlorpicrin 75/25 | soil fumigation at 300 lbs./ac via injection prior to transplanting, no HP-1000 ™ treatments applied. |
| Telone/chlorpicrin 70/30 | soil fumigation at 45 gal./ac via injection prior to transplanting, no HP-1000 ™ treatments applied. |
| untreated control (UTC) | no fumigation, no HP-1000 ™ treatments |

[1]Non-fumigated soil had been cropped to vetch for the two previous years.

Transplanting was done in late fall when cool weather tended to slow plant growth. Two weeks after transplanting, the first foliar application of HP-1000™ was made at 40 µg/ml (a.i.) with a back-pack sprayer. Three weeks after transplanting, preliminary results were gathered comparing HP-1000™ treatment against methyl bromide and UTC by counting the number of flowers on all strawberry "plug" plants in each replication. Since flowering had not yet occurred in the "bare-root" plants, each plant in replicates for this treatment was assessed for early leaf growth by measuring the distance from leaf tip to stem on the middle leaf of 3-leaf cluster. Results (Tables 37 and 38) indicated that treatment with HP-1000™ provided early enhanced flower growth and leaf size for "plug" and "bare-root" strawberry plants, respectively.

TABLE 37

Earlier flowering of "plug" strawberry transplants after foliar treatments with HP-1000 ™.

| Treatment | Rate (a.i.) | No. flowers/ rep[1] | % above UTC |
|---|---|---|---|
| UTC | — | 2.0 a | — |
| HP-1000 ™ | 40 µg/ml | 7.5 b | 275 |
| Methyl bromide/ chlorpicrin | 300 lbs./ac | 5.3 b | 163 |

[1]Means followed by different letters are significantly different according to Duncan's MRT, P = 0.05.

TABLE 38

Increased leaf growth in "bare-root" strawberry transplants after foliar treatments with HP-1000 ™.

| Treatment | Rate (a.i.) | Leaf length[1] (in.) | % above UTC |
|---|---|---|---|
| UTC | — | 1.26 a | — |
| HP-1000 ™ | 40 µg/ml | 1.81 b | 44 |

[1]Means followed by different letters are significantly different according to Duncan's MRT, P = 0.05.

Example 20
Early Growth Enhancement of Jalapeño Peppers from Application of HP-1000™

Jalapeño pepper (cv. Mittlya) transplants were treated with a root drench of HP-1000 (EDEN Bioscience) (*Erwinia amylovora* hypersensitive response elicitor formulation) (30 μg/ml a.i.) for 1 hour, then transplanted into randomized field plots replicated four times. An untreated control (UTC) was also included. Beginning 14 days after transplanting, treated plants received three foliar sprays of HP-1000™ at 14 day intervals using a back-pack sprayer. One week after the third application of HP-1000™ (54 days after transplanting), plant height was measured from four randomly selected plants per replication. Results from these measurements indicated that the HP-1000™ treated plants were approximately 26% taller than the UTC plants (Table 39). In addition, the number of buds, flowers or fruit on each plant was counted. These results indicated that the HP-1000™ treated plants had over 61% more flowers, fruit or buds compared to UTC plants (Table 40).

TABLE 39

Increased plant height in Jalapeño peppers after treatments with HP-1000 ™.

| Treatment | Rate (a.i.) | Plant Ht. (in.)[1] | % above UTC |
|---|---|---|---|
| UTC | — | a 7.0 | — |
| HP-1000 ™ | 30 μg/ml | 8.6 b | 23.6 |

[1]Means followed by different letters are significantly different according to Duncan's MRT, P = 0.05.

TABLE 40

Increased number of flowers, fruit or buds in Jalapeño peppers after treatments with HP-1000 ™.

| Treatment | Rate (a.i.) | No. flowers, fruit or buds/plant[1] | % above UTC |
|---|---|---|---|
| UTC | — | 20.6 a | — |
| HP-1000 ™ | 30 μg/ml | 12.8 b | 61.3 |

[1]Means followed by different letters are significantly different according to Duncan's MRT, P = 0.05.

Example 21

Growth Enhancement of Tobacco from Application of HP-1000™

Tobacco seedlings were transplanted into randomized field plots replicated three times. A foliar spray of HP-1000™ (EDEN Bioscience) (*Erwinia amylovora* hypersensitive response elicitor formulation) was applied after transplanting at one of three rates: 15, 30, or 60 μg/ml a.i. Sixty days later, a second foliar application of HP-1000 was made. Two days after the second application, plant height, number of leaves per plant, and the leaf size (area) were measured from ten, randomly selected plants per treatment. Results from these measurements indicated treatment with HP-1000™ enhanced tobacco plant growth significantly (Tables 41, 42, and 43). Plant height was increased by 6–13%, while plants treated with HP-1000™ at 30 and 60 μg/ml averaged just over 1 more leaf per plant than UTC. Most significantly, however, treatment with HP-1000™ at 15, 30, and 60 μg/ml resulted in corresponding increases in leaf area. Tobacco plants with an extra leaf per plant and an increase in average leaf size (area) represent a commercially significant response.

TABLE 41

Increased plant height in tobacco after treatment with HP-1000 ™.

| Treatment | Rate (a.i.) | Plant Ht. (cm) | % above UTC |
|---|---|---|---|
| UTC | — | 72.0 | — |
| HP-1000 ™ | 15 μg/ml | 76.4 | 5.3 |
| HP-1000 ™ | 30 μg/ml | 79.2 | 9.0 |
| HP-1000 ™ | 60 μg/ml | 81.3 | 6.9 |

TABLE 42

Increased number of tobacco leaves per plant after treatment with HP-1000 ™.

| Treatment | Rate (a.i.) | Leaves/ plant[1] | % above UTC |
|---|---|---|---|
| UTC | — | 16.8 | — |
| HP-1000 ™ | 15 μg/ml | 17.4 | 3.6 |
| HP-1000 ™ | 30 μg/ml | 18.1 | 7.7 |
| HP-1000 ™ | 60 μg/ml | 17.9 | 6.5 |

TABLE 43

Increased leaf area in tobacco after treatment with HP-1000 ™.

| Treatment | Rate (a.i.) | Leaf area ($cm^2$) | % above UTC |
|---|---|---|---|
| UTC | — | 1,246 | — |
| HP-1000 ™ | 15 μg/ml | 1,441 | 16 |
| HP-1000 ™ | 30 μg/ml | 1,543 | 24 |
| HP-1000 ™ | 60 μg/ml | 1,649 | 32 |

Example 22

Growth Enhancement of Winter Wheat from Application of HP-1000™

Winter wheat seed was "dusted" with dry HP-1000™ (EDEN Bioscience) (*Erwinia amylovora* hypersensitive response elicitor formulation) powder at the rate of 3 ounces of formulated product (3% a.i.) per 100 lbs. seed, then planted using conventional seeding equipment into randomized test plots 11.7 feet by 100 feet long. Additional treatments included a seed "dusting" with HP-1000™ powder (3% a.i.) at 1 oz. formulated product per 100 lbs. seed, a seed-soak in a solution of HP-1000™ at a concentration of 20 μg/ml, a.i., for four hours, then air-dried before planting, a standard chemical (Dividend®) fungicide "dusting", and an untreated control (UTC). Eight days after planting, HP-1000™ treated seeds began to emerge, whereas the UTC and chemical standard-treated seed did not emerge until approximately 14 days after planting, the normal time expected. At 41 days after planting, seedlings were removed from the ground and evaluated. Root mass for wheat treated with HP-1000™ as a "dusting" at 3 oz./100 lb. was visually inspected and judged to be approximately twice as great as any of the other treatments.

Following the field trial, a greenhouse experiment was designed to gain confirmation of these results. Treatments included wheat seed dusted with dry HP-1000™ (10% a.i.) at a rate of 3 ounces per 100 lbs. of seed, seed soaking of HP-1000™ in solution concentration of 20 mg/ml for four hours before planting, and an untreated control (UTC). Wheat seeds from each treatment were planted at the rate of 25 seeds per pot, with five pots serving as replicates for each treatment. Fifteen days after planting, ten randomly selected seedlings from each treatment pot were removed, carefully cleaned, and measured for root length. Since the above-ground portion of individual seedlings did not exhibit any treatment effect, increased root growth from treatment with HP-1000™ did not influence the selection of samples. The increase in root growth from either HP-1000™ treatment was significantly greater than UTC (Table 49); however, the seed dusting treatment appeared to give slightly better results.

TABLE 44

Increased root growth in wheat seedlings after treatment with HP-1000 ™.

| Treatment | Rate | Root length (cm)[1] | % above UTC |
|---|---|---|---|
| UTC | — | 35.6 a | — |
| HP-1000 ™ (dusting) | 3 oz./100 lbs | 41.0 b | 17.4 |
| HP-1000 ™ (soaking) | 20 μg/ml | 40.8 b | 14.6 |

[1]Means followed by different letters are significantly different according to Duncan's MRT, P = 0.05.

Example 23

Growth Enhancement of Cucumbers from Application of HP-1000™

A field trial of commercially produced cucumbers consisted of four treatments, HP-1000™ (EDEN Bioscience) (*Erwinia amylovora* hypersensitive response elicitor formulation) at two rates (20 or 40 μg/ml), a chemical standard for disease control (Bravo® (Zeneca Ag Products, Wilmington, Del.) +Maneb®) and an untreated control (UTC). Each treatment was replicated four times in 3×75 foot plots with a plant spacing of approximately 2 feet for each treatment. Foliar sprays of HP-1000™ were applied beginning at first true leaf and repeated at 14 day intervals until the last harvest for a total of six applications. The standard fungicide mix was applied every seven days or sooner if conditions warranted. Commercial harvesting began approximately two months after first application of HP-1000υ (after five sprays of HP-1000™ had been applied), and a final harvest was made approximately 14 days after the first harvest.

Results from the first harvest indicated that treatment with HP-1000™ enhanced the average cucumber yield by increasing the total number of cucumbers harvested and not the average weight of individual cucumbers (Tables 45–47). The same trend was noted at the final harvest (Tables 48–49). It was commercially important that the yield increase resulting from treatment with HP-1000™ was not achieved by significantly increasing average cucumber size.

TABLE 45

Increased cucumber yield after treatment with HP-1000 ™, first harvest.

| Treatment | Rate (a.i.) | Yield/trt[1] (kg.) | % above UTC |
|---|---|---|---|
| UTC | — | 10.0 a | — |
| Bravo + Maneb | label | 10.8 a | 8.4 |

TABLE 45-continued

Increased cucumber yield after treatment with HP-1000 ™, first harvest.

| Treatment | Rate (a.i.) | Yield/trt[1] (kg.) | % above UTC |
|---|---|---|---|
| HP-1000 ™ | 20 μg/ml | 12.3 ab | 22.8 |
| HP-1000 ™ | 40 μg/ml | 13.8 b | 38.0 |

[1]Means followed by different letters are significantly different according to Duncan's MRT, P = 0.05.

TABLE 46

Increased number of fruit in cucumbers after treatment with HP-1000 ™, first harvest.

| Treatment | Rate (a.i.) | No. fruit/ trt[1] | % above UTC |
|---|---|---|---|
| UTC | — | 24.5 a | — |
| Bravo + Maneb | label | 27.6 ab | 12.8 |
| HP-1000 ™ | 20 μg/ml | 31.2 b | 27.0 |
| HP-1000 ™ | 40 μg/ml | 34.3 b | 39.8 |

[1]Means followed by different letters are significantly different according to Duncan's MRT, P = 0.05.

TABLE 47

Average weight of cucumbers after treatment with HP-1000 ™, first harvest.

| Treatment | Rate (a.i.) | Weight/ fruit (g) | % change vs. UTC |
|---|---|---|---|
| UTC | — | 406 | — |
| Bravo + Maneb | label | 390 | −4 |
| HP-1000 ™ | 20 μg/ml | 395 | −3 |
| HP-1000 ™ | 40 μg/ml | 403 | −1 |

TABLE 48

Increased cucumber yield after treatment with HP-1000 ™, third harvest.

| Treatment | Rate (a.i.) | Yield/trt[1] (kg.) | % above UTC |
|---|---|---|---|
| UTC | — | 17.5 a | — |
| Bravo + Maneb | label | 14.0 b | −20.1 |
| HP-1000 ™ | 20 μg/ml | 20.1 a | 15.3 |
| HP-1000 ™ | 40 μg/ml | 20.2 a | 15.6 |

[1]Means followed by different letters are significantly different according to Duncan's MRT, P = 0.05.

TABLE 49

Increased number of fruit in cucumbers after treatment with HP-1000 ™, third harvest.

| Treatment | Rate (a.i.) | No. fruit/ trt[1] | % change vs. UTC |
|---|---|---|---|
| UTC | — | 68.8 ab | — |
| Bravo + Maneb | label | 60.0 a | −12.7 |
| HP-1000 ™ | 20 μg/ml | 82.3 b | 19.6 |
| HP-1000 ™ | 40 μg/ml | 85.3 b | 24.0 |

[1]Means followed by different letters are significantly different according to Duncan's MRT, P = 0.05.

TABLE 50

Average weight of cucumbers after treatment with HP-1000 ™, third harvest.

| Treatment | Rate (a.i.) | Weight/ fruit (g) | % change vs. UTC |
|---|---|---|---|
| UTC | — | 255 | — |
| Bravo + Maneb | label | 232 | −9 |
| HP-1000 ™ | 20 µg/ml | 247 | −3 |
| HP-1000 ™ | 40 µg/ml | 237 | −7 |

Example 24

Harpin$_{pss}$ from *Pseudomonas syringae* pv syringae Induces Growth Enhancement in Tomato To test if harpin$_{pss}$ (i.e. the hypersensitive response elicitor from *Pseudomonas syringae* pv syringae) (He, S. Y., et al., "*Pseudomonas syringae* pv syringae Harpin$_{pss}$. A Protein that is Secreted via the Hrp Pathway and Elicits the Hypersensitive Response in Plants," Cell 73:1255–66 (1993), which is hereby incorporated by reference) also stimulates plant growth, tomato seeds (Marglobe variety) were sowed in 8 inches pots with artificial soil. 10 days after sowing, the seedlings were transplanted into individual pots. Throughout the experiment, fertilizer, irrigation of water, temperature, and soil moisture were maintained uniformly among plants. 16 days after transplanting, the initial plant height was measured and the first application of harpin$_{pss}$ was made, this is referred to as day 0. A second application was made on day 15. Additional growth data was collected on day 10 and day 30. The final data collection on day 30 included both plant height and fresh weight.

The harpin$_{pss}$ used for application during the experiment was produced by fermenting *E. coli* DH5 containing the plasmid with the gene encoding harpin$_{pss}$ (i.e. hrpZ). The cells were harvested, resuspended in 5 mM potassium phosphate buffer, and disrupted by sonication. The sonicated material was boiled for 5 minutes and then centrifugated for 10 min. at 10,000 rpm. The supernatant was considered as Cell-Free Elicitor Preparation (CFEP). 20 and 50 µg/ml harpinpss solution was made with the same buffer used to make cell suspension. CFEP prepared from the same strain containing the same plasmid but without hrpZ gene was used as the material for control treatment.

The wetting agent, Pinene II (Drexel Chemical Co., Memphis, Tenn.) was added to the harpin$_{pss}$ solution at the concentration of 0.1%, then harpin$_{pss}$ was sprayed onto tomato plant until there was run off.

Table 51 shows that there was a significant difference between the harpin$_{pss}$ treatment groups and the control group. Harpin$_{pss}$ treated tomato increased more than 10% in height. The data supports the claim that harpin$_{pss}$ does act similar to the hypersensitive response elicitor from *Erwinia amylovora*, in that when applied to tomato and many other species of plants, there is a growth enhancement effect. In addition to a significant increase of tomato height harpin$_{pss}$-treated tomato had more biomass, big leaves, early flower setting, and over all healthier appearance.

TABLE 51

| Harpin$_{pss}$ enhances the growth of tomato plant | | | |
|---|---|---|---|
| | Plant Height (cm[1]) | | |
| Treatment | Day 0 | Day 10 | Day 30 |
| CFEP Control | 8.5[2] (0.87) a[3] | 23.9 (1.90) a | 68.2 (8.60) a |
| Harpinpss 20 μg/ml | 8.8 (0.98) a | 27.3 (1.75) b | 74.2 (6.38) b |
| Harpinpss 50 μg/ml | 8.8 (1.13) a | 26.8 (2.31) b | 75.4 6.30) b |

[1]Plant height was measured to the nearest 0.5 cm. Day 0 refers to the day the initial plant heights were recorded and the first application was made.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method of enhancing growth in plants compared to untreated plants comprising:
applying a hypersensitive response elicitor polypeptide or protein in a non-infectious form to a plant or plant seed under conditions effective to enhance growth of the plant or plants grown from the plant seed, compared to an untreated plant or plant seed, wherein the hypersensitive response elicitor protein or polypeptide is heat stable, glycine rich, and contains no cysteine.

2. A method according to claim 1, wherein the hypersensitive response elicitor polypeptide or protein is in isolated form.

3. A method according to claim 2, wherein the hypersensitive response elicitor polypeptide or protein corresponds to that derived from a pathogen selected from the group consisting of Erwinia, Pseudomonas, Xanthomonas, and mixtures thereof.

4. A method according to claim 3, wherein the hypersensitive response elicitor polypeptide or protein corresponds to that derived from *Erwinia chrysanthemum*.

5. A method according to claim 3, wherein the hypersensitive response elicitor polypeptide or protein corresponds to that derived from *Erwinia amylovora*.

6. A method according to claim 3, wherein the hypersensitive response elicitor polypeptide or protein corresponds to that derived from *Pseudomonas syringae*.

7. A method according to claim 3, wherein the hypersensitive response elicitor polypeptide or protein corresponds to that derived from *Pseudomonas solanacearum*.

8. A method according to claim 3, wherein the hypersensitive response elicitor polypeptide or protein corresponds to that derived from *Xanthomonas campestris*.

9. A method according to claim 2, wherein the plant is selected from the group consisting of dicots and monocots.

10. A method according to claim 9, wherein the plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

11. A method according to claim 9, wherein the plant is selected from the group consisting of rose, Saintpaulia, petunia, pelargonium, poinsettia, chrysanthemum, carnation, and zinnia.

12. A method according to claim 2, wherein plants are treated during said applying which is carried out by spraying, injection, or leaf abrasion at a time proximate to when said applying takes place.

13. A method according to claim 2, wherein plant seeds are treated during said applying which is carried out by spraying, injection, coating, dusting, or immersion.

14. A method according to claim 2, wherein the hypersensitive response elicitor polypeptide or protein is applied to plants or plant seeds as a composition further comprising a carrier.

15. A method according to claim 14, wherein the carrier is selected from the group consisting of water, aqueous solutions, slurries, and powders.

16. A method according to claim 14, wherein the composition contains greater than 0.5 nM of the hypersensitive response elicitor polypeptide or protein.

17. A method according to claim 14, wherein the composition further contains additives selected from the group consisting of fertilizer, insecticide, fungicide, nematacide, and mixtures thereof.

18. A method according to claim 2, wherein said applying causes infiltration of the polypeptide or protein into the plant.

19. A method according to claim 2, wherein said applying effects increased plant height, compared to an untreated plant or plant seed.

20. A method according to claim 19, wherein plants are treated during said applying.

21. A method according to claim 19, wherein plant seeds are treated during said applying, said method further comprising:
planting the seeds treated with the hypersensitive response elicitor in natural or artificial soil and propagating the plants from the seeds planted in the soil.

22. A method according to claim 2, wherein plant seeds are treated during said applying to increase plant seed quantities which germinate, said method further comprising:

planting the seeds treated with the hypersensitive response elicitor protein or polypeptide in natural or artificial soil and propagating plants from the seeds planted in the soil.

23. A method according to claim 2, wherein said applying effects greater yield, compared to an untreated plant or plant seed.

24. A method according to claim 23, wherein plants are treated during said applying.

25. A method according to claim 23, wherein plant seeds are treated during said applying, said method further comprising:

planting the seeds treated with the hypersensitive response elicitor protein or polypeptide in natural or artificial soil and propagating plants from the seeds planted in the soil.

26. A method according to claim 2, wherein said applying effects earlier germination, compared to an untreated plant or plant seed.

27. A method according to claim 26, wherein plant seeds are treated during said applying, said method further comprising:

planting the seeds treated with the hypersensitive response elicitor protein or polypeptide in natural or artificial soil and propagating plants from the seeds planted in the soil.

28. A method according to claim 2, wherein said applying effects earlier maturation, compared to an untreated plant or plant seed.

29. A method according to claim 28, wherein plants are treated during said applying.

30. A method according to claim 28, wherein plant seeds are treated during said applying, said method further comprising:

planting the seeds treated with the hypersensitive response elicitor protein or polypeptide in natural or artificial soil and propagating plants from the seeds planted in the soil.

31. A method according to claim 2, wherein plant seeds are treated during said applying, said method further comprising:

planting the seeds treated with the hypersensitive response elicitor protein or polypeptide in natural or artificial soil and propagating plants from the seeds planted in the soil.

32. A method according to claim 31 further comprising:

applying the hypersensitive response elicitor protein or polypeptide in a non-infectious form to the propagated plants to enhance growth further.

33. A method according to claim 2, wherein said applying effects earlier fruit and plant coloration, compared to an untreated plant of plant seed.

34. A method according to claim 33, wherein plant seeds are treated during said applying, said method further comprising:

planting the seeds treated with the hypersensitive response elicitor protein or polypeptide in natural or artificial soil and propagating plants from the seeds planted in the soil.

35. A method of enhancing growth in plants compared to untreated plants comprising:

applying a hypersensitive response elicitor polypeptide or protein, corresponding to that derived from a Phylophthora species, in a non-infectious form, to a plant or plant seed under conditions effective to enhance growth of the plant of plants grown from the plant seed, compared to an untreated plant or plant seed.

* * * * *

SEQUENCE LISTING

```
(1) GENERAL INFORMATION:

(iii) NUMBER OF SEQUENCES: 10

(2) INFORMATION FOR SEQ ID NO:1:

(i) SEQUENCE CHARACTERISTICS:
          (A) LENGTH: 338 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:1:

Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45
```

```
Ser Ala Leu Thr Ser Met Met Phe Gly Ala Leu Ala Gln Gly Leu
 50                  55                  60

Gly Ala Ser Ser Lys Gly Leu Gly Met Ser Asn Gln Leu Gly Gln Ser
 65                  70                  75                  80

Phe Gly Asn Gly Ala Gln Gly Ala Ser Asn Leu Leu Ser Val Pro Lys
                 85                  90                  95

Ser Gly Gly Asp Ala Leu Ser Lys Met Phe Asp Lys Ala Leu Asp Asp
                100                 105                 110

Leu Leu Gly His Asp Thr Val Thr Lys Leu Thr Asn Gln Ser Asn Gln
            115                 120                 125

Leu Ala Asn Ser Met Leu Asn Ala Ser Gln Met Thr Gln Gly Asn Met
130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
                180                 185                 190

Gly Asn Ala Ile Gly Met Gly Val Gly Gln Asn Ala Ala Leu Ser Ala
            195                 200                 205

Leu Ser Asn Val Ser Thr His Val Asp Gly Asn Asn Arg His Phe Val
210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
                260                 265                 270

Pro Asp Asp Asp Gly Met Thr Gly Ala Ser Met Asp Lys Phe Arg Gln
            275                 280                 285

Ala Met Gly Met Ile Lys Ser Ala Val Ala Gly Asp Thr Gly Asn Thr
290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

(2) INFORMATION FOR SEQ ID NO:2:

(i) SEQUENCE CHARACTERISTICS:
        (A) LENGTH: 2141 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
CGATTTTACC CGGGTGAACG TGCTATGACC GACAGCATCA CGGTATTCGA CACCGTTACG      60

GCGTTTATGG CCGCGATGAA CCGGCATCAG GCGGCGCGCT GGTCGCCGCA ATCCGGCGTC     120

GATCTGGTAT TTCAGTTTGG GGACACCGGG CGTGAACTCA TGATGCAGAT TCAGCCGGGG     180

CAGCAATATC CCGGCATGTT GCGCACGCTG CTCGCTCGTC GTTATCAGCA GGCGGCAGAG     240

TGCGATGGCT GCCATCTGTG CCTGAACGGC AGCGATGTAT TGATCCTCTG GTGGCCGCTG     300
```

-continued

```
CCGTCGGATC CCGGCAGTTA TCCGCAGGTG ATCGAACGTT TGTTTGAACT GGCGGGAATG      360

ACGTTGCCGT CGCTATCCAT AGCACCGACG GCGCGTCCGC AGACAGGGAA CGGACGCGCC      420

CGATCATTAA GATAAAGGCG GCTTTTTTTA TTGCAAAACG GTAACGGTGA GGAACCGTTT      480

CACCGTCGGC GTCACTCAGT AACAAGTATC CATCATGATG CCTACATCGG GATCGGCGTG      540

GGCATCCGTT GCAGATACTT TTGCAACAC CTGACATGAA TGAGGAAACG AAATTATGCA       600

AATTACGATC AAAGCGCACA TCGGCGGTGA TTTGGGCGTC TCCGGTCTGG GGCTGGGTGC      660

TCAGGGACTG AAAGGACTGA ATTCCGCGGC TTCATCGCTG GGTTCCAGCG TGGATAAACT      720

GAGCAGCACC ATCGATAAGT TGACCTCCGC GCTGACTTCG ATGATGTTTG GCGGCGCGCT      780

GGCGCAGGGG CTGGGCGCCA GCTCGAAGGG GCTGGGGATG AGCAATCAAC TGGGCCAGTC      840

TTTCGGCAAT GGCGCGCAGG GTGCGAGCAA CCTGCTATCC GTACCGAAAT CCGGCGGCGA      900

TGCGTTGTCA AAAATGTTTG ATAAAGCGCT GGACGATCTG CTGGGTCATG ACACCGTGAC      960

CAAGCTGACT AACCAGAGCA ACCAACTGGC TAATTCAATG CTGAACGCCA GCCAGATGAC     1020

CCAGGGTAAT ATGAATGCGT TCGGCAGCGG TGTGAACAAC GCACTGTCGT CCATTCTCGG     1080

CAACGGTCTC GGCCAGTCGA TGAGTGGCTT CTCTCAGCCT TCTCTGGGGG CAGGCGGCTT     1140

GCAGGGCCTG AGCGGCGCGG GTGCATTCAA CCAGTTGGGT AATGCCATCG GCATGGGCGT     1200

GGGGCAGAAT GCTGCGCTGA GTGCGTTGAG TAACGTCAGC ACCCACGTAG ACGGTAACAA     1260

CCGCCACTTT GTAGATAAAG AAGATCGCGG CATGGCGAAA GAGATCGGCC AGTTTATGGA     1320

TCAGTATCCG GAAATATTCG GTAAACCGGA ATACCAGAAA GATGGCTGGA GTTCGCCGAA     1380

GACGGACGAC AAATCCTGGG CTAAAGCGCT GAGTAAACCG GATGATGACG GTATGACCGG     1440

CGCCAGCATG GACAAATTCC GTCAGGCGAT GGGTATGATC AAAAGCGCGG TGGCGGGTGA     1500

TACCGGCAAT ACCAACCTGA ACCTGCGTGG CGCGGGCGGT GCATCGCTGG GTATCGATGC     1560

GGCTGTCGTC GGCGATAAAA TAGCCAACAT GTCGCTGGGT AAGCTGGCCA ACGCCTGATA     1620

ATCTGTGCTG GCCTGATAAA GCGGAAACGA AAAAGAGAC GGGGAAGCCT GTCTCTTTTC      1680

TTATTATGCG GTTTATGCGG TTACCTGGAC CGGTTAATCA TCGTCATCGA TCTGGTACAA     1740

ACGCACATTT TCCCGTTCAT TCGCGTCGTT ACGCGCCACA ATCGCGATGG CATCTTCCTC     1800

GTCGCTCAGA TTGCGCGGCT GATGGGGAAC GCCGGGTGGA ATATAGAGAA ACTCGCCGGC     1860

CAGATGGAGA CACGTCTGCG ATAAATCTGT GCCGTAACGT GTTTCTATCC GCCCCTTTAG     1920

CAGATAGATT GCGGTTTCGT AATCAACATG GTAATGCGGT TCCGCCTGTG CGCCGGCCGG     1980

GATCACCACA ATATTCATAG AAAGCTGTCT TGCACCTACC GTATCGCGGG AGATACCGAC     2040

AAAATAGGGC AGTTTTTGCG TGGTATCCGT GGGGTGTTCC GGCCTGACAA TCTTGAGTTG     2100

GTTCGTCATC ATCTTTCTCC ATCTGGGCGA CCTGATCGGT T                         2141
```

(2) INFORMATION FOR SEQ ID NO:3:

(i) SEQUENCE CHARACTERISTICS:
        (A) LENGTH: 403 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ser Leu Asn Thr Ser Gly Leu Gly Ala Ser Thr Met Gln Ile Ser
 1               5                  10                  15

Ile Gly Gly Ala Gly Gly Asn Asn Gly Leu Leu Gly Thr Ser Arg Gln
```

```
                    20                  25                  30
Asn Ala Gly Leu Gly Gly Asn Ser Ala Leu Gly Leu Gly Gly Asn
                35                  40                  45
Gln Asn Asp Thr Val Asn Gln Leu Ala Gly Leu Leu Thr Gly Met Met
 50                  55                  60
Met Met Met Ser Met Met Gly Gly Gly Leu Met Gly Gly Gly Leu
 65                  70                  75                  80
Gly Gly Gly Leu Gly Asn Gly Leu Gly Gly Ser Gly Gly Leu Gly Glu
                 85                  90                  95
Gly Leu Ser Asn Ala Leu Asn Asp Met Leu Gly Gly Ser Leu Asn Thr
                100                 105                 110
Leu Gly Ser Lys Gly Gly Asn Asn Thr Thr Ser Thr Thr Asn Ser Pro
                115                 120                 125
Leu Asp Gln Ala Leu Gly Ile Asn Ser Thr Ser Gln Asn Asp Asp Ser
130                 135                 140
Thr Ser Gly Thr Asp Ser Thr Ser Asp Ser Ser Asp Pro Met Gln Gln
145                 150                 155                 160
Leu Leu Lys Met Phe Ser Glu Ile Met Gln Ser Leu Phe Gly Asp Gly
                165                 170                 175
Gln Asp Gly Thr Gln Gly Ser Ser Ser Gly Gly Lys Gln Pro Thr Glu
                180                 185                 190
Gly Glu Gln Asn Ala Tyr Lys Lys Gly Val Thr Asp Ala Leu Ser Gly
                195                 200                 205
Leu Met Gly Asn Gly Leu Ser Gln Leu Leu Gly Asn Gly Gly Leu Gly
                210                 215                 220
Gly Gly Gln Gly Gly Asn Ala Gly Thr Gly Leu Asp Gly Ser Ser Leu
225                 230                 235                 240
Gly Gly Lys Gly Leu Gln Asn Leu Ser Gly Pro Val Asp Tyr Gln Gln
                245                 250                 255
Leu Gly Asn Ala Val Gly Thr Gly Ile Gly Met Lys Ala Gly Ile Gln
                260                 265                 270
Ala Leu Asn Asp Ile Gly Thr His Arg His Ser Ser Thr Arg Ser Phe
                275                 280                 285
Val Asn Lys Gly Asp Arg Ala Met Ala Lys Glu Ile Gly Gln Phe Met
                290                 295                 300
Asp Gln Tyr Pro Glu Val Phe Gly Lys Pro Gln Tyr Gln Lys Gly Pro
305                 310                 315                 320
Gly Gln Glu Val Lys Thr Asp Asp Lys Ser Trp Ala Lys Ala Leu Ser
                325                 330                 335
Lys Pro Asp Asp Asp Gly Met Thr Pro Ala Ser Met Glu Gln Phe Asn
                340                 345                 350
Lys Ala Lys Gly Met Ile Lys Arg Pro Met Ala Gly Asp Thr Gly Asn
                355                 360                 365
Gly Asn Leu Gln Ala Arg Gly Ala Gly Gly Ser Ser Leu Gly Ile Asp
                370                 375                 380
Ala Met Met Ala Gly Asp Ala Ile Asn Asn Met Ala Leu Gly Lys Leu
385                 390                 395                 400
Gly Ala Ala
```

(2) INFORMATION FOR SEQ ID NO:4:

(i) SEQUENCE CHARACTERISTICS:
        (A) LENGTH: 1288 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:4:

```
AAGCTTCGGC ATGGCACGTT TGACCGTTGG GTCGGCAGGG TACGTTTGAA TTATTCATAA      60
GAGGAATACG TTATGAGTCT GAATACAAGT GGGCTGGGAG CGTCAACGAT GCAAATTTCT     120
ATCGGCGGTG CGGGCGGAAA TAACGGGTTG CTGGGTACCA GTCGCCAGAA TGCTGGGTTG     180
GGTGGCAATT CTGCACTGGG GCTGGGCGGC GGTAATCAAA ATGATACCGT CAATCAGCTG     240
GCTGGCTTAC TCACCGGCAT GATGATGATG ATGAGCATGA TGGGCGGTGG TGGGCTGATG     300
GGCGGTGGCT TAGGCGGTGG CTTAGGTAAT GGCTTGGGTG GCTCAGGTGG CCTGGGCGAA     360
GGACTGTCGA ACGCGCTGAA CGATATGTTA GGCGGTTCGC TGAACACGCT GGGCTCGAAA     420
GGCGGCAACA ATACCACTTC AACAACAAAT TCCCCGCTGG ACCAGGCGCT GGGTATTAAC     480
TCAACGTCCC AAAACGACGA TTCCACCTCC GGCACAGATT CCACCTCAGA CTCCAGCGAC     540
CCGATGCAGC AGCTGCTGAA GATGTTCAGC GAGATAATGC AAAGCCTGTT TGGTGATGGG     600
CAAGATGGCA CCCAGGGCAG TTCCTCTGGG GGCAAGCAGC CGACCGAAGG CGAGCAGAAC     660
GCCTATAAAA AAGGAGTCAC TGATGCGCTG TCGGGCCTGA TGGGTAATGG TCTGAGCCAG     720
CTCCTTGGCA ACGGGGACT  GGGAGGTGGT CAGGGCGGTA ATGCTGGCAC GGGTCTTGAC     780
GGTTCGTCGC TGGGCGGCAA AGGGCTGCAA AACCTGAGCG GCCGGTGGA  CTACCAGCAG     840
TTAGGTAACG CCGTGGGTAC CGGTATCGGT ATGAAAGCGG GCATTCAGGC GCTGAATGAT     900
ATCGGTACGC ACAGGCACAG TTCAACCCGT TCTTTCGTCA ATAAAGGCGA TCGGGCGATG     960
GCGAAGGAAA TCGGTCAGTT CATGGACCAG TATCCTGAGG TGTTTGGCAA GCCGCAGTAC    1020
CAGAAAGGCC CGGGTCAGGA GGTGAAAACC GATGACAAAT CATGGGCAAA AGCACTGAGC    1080
AAGCCAGATG ACGACGGAAT GACACCAGCC AGTATGGAGC AGTTCAACAA AGCCAAGGGC    1140
ATGATCAAAA GGCCCATGGC GGGTGATACC GGCAACGGCA ACCTGCAGGC ACGCGGTGCC    1200
GGTGGTTCTT CGCTGGGTAT TGATGCCATG ATGGCCGGTG ATGCCATTAA CAATATGGCA    1260
CTTGGCAAGC TGGGCGCGGC TTAAGCTT                                      1288
```

(2) INFORMATION FOR SEQ ID NO:5:

(i) SEQUENCE CHARACTERISTICS:
        (A) LENGTH: 341 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Lys Leu Ala Glu Glu Leu Met
         35                  40                  45

Arg Asn Gly Gln Leu Asp Asp Ser Ser Pro Leu Gly Lys Leu Leu Ala
         50                  55                  60

Lys Ser Met Ala Ala Asp Gly Lys Ala Gly Gly Ile Glu Asp Val
 65                  70                  75                  80
```

```
Ile Ala Ala Leu Asp Lys Leu Ile His Glu Lys Leu Gly Asp Asn Phe
                 85                  90                  95
Gly Ala Ser Ala Asp Ser Ala Ser Gly Thr Gly Gln Gln Asp Leu Met
            100                 105                 110
Thr Gln Val Leu Asn Gly Leu Ala Lys Ser Met Leu Asp Asp Leu Leu
        115                 120                 125
Thr Lys Gln Asp Gly Gly Thr Ser Phe Ser Glu Asp Asp Met Pro Met
    130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
                165                 170                 175
Leu Asp Gly Asp Glu Thr Ala Ala Phe Arg Ser Ala Leu Asp Ile Ile
            180                 185                 190
Gly Gln Gln Leu Gly Asn Gln Gln Ser Asp Ala Gly Ser Leu Ala Gly
        195                 200                 205
Thr Gly Gly Leu Gly Thr Pro Ser Ser Phe Ser Asn Asn Ser Ser
    210                 215                 220
Val Met Gly Asp Pro Leu Ile Asp Ala Asn Thr Gly Pro Gly Asp Ser
225                 230                 235                 240
Gly Asn Thr Arg Gly Glu Ala Gly Gln Leu Ile Gly Glu Leu Ile Asp
                245                 250                 255
Arg Gly Leu Gln Ser Val Leu Ala Gly Gly Leu Gly Thr Pro Val
            260                 265                 270
Asn Thr Pro Gln Thr Gly Thr Ser Ala Asn Gly Gly Gln Ser Ala Gln
        275                 280                 285
Asp Leu Asp Gln Leu Leu Gly Gly Leu Leu Leu Lys Gly Leu Glu Ala
    290                 295                 300
Thr Leu Lys Asp Ala Gly Gln Thr Gly Thr Asp Val Gln Ser Ser Ala
305                 310                 315                 320
Ala Gln Ile Ala Thr Leu Leu Val Ser Thr Leu Leu Gln Gly Thr Arg
                325                 330                 335
Asn Gln Ala Ala Ala
            340

(2) INFORMATION FOR SEQ ID NO:6:

(i) SEQUENCE CHARACTERISTICS:
        (A) LENGTH: 1026 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

ATGCAGAGTC TCAGTCTTAA CAGCAGCTCG CTGCAAACCC CGGCAATGGC CCTTGTCCTG      60

GTACGTCCTG AAGCCGAGAC GACTGGCAGT ACGTCGAGCA AGGCGCTTCA GGAAGTTGTC     120

GTGAAGCTGG CCGAGGAACT GATGCGCAAT GGTCAACTCG ACGACAGCTC GCCATTGGGA     180

AAACTGTTGG CCAAGTCGAT GGCCGCAGAT GGCAAGGCGG GCGGCGGTAT TGAGGATGTC     240

ATCGCTGCGC TGGACAAGCT GATCCATGAA AAGCTCGGTG ACAACTTCGG CGCGTCTGCG     300

GACAGCGCCT CGGGTACCGG ACAGCAGGAC CTGATGACTC AGGTGCTCAA TGGCCTGGCC     360

AAGTCGATGC TCGATGATCT TCTGACCAAG CAGGATGGCG GGACAAGCTT CTCCGAAGAC     420

GATATGCCGA TGCTGAACAA GATCGCGCAG TTCATGGATG ACAATCCCGC ACAGTTTCCC     480
```

-continued

```
AAGCCGGACT CGGGCTCCTG GGTGAACGAA CTCAAGGAAG ACAACTTCCT TGATGGCGAC      540

GAAACGGCTG CGTTCCGTTC GGCACTCGAC ATCATTGGCC AGCAACTGGG TAATCAGCAG      600

AGTGACGCTG GCAGTCTGGC AGGGACGGGT GGAGGTCTGG GCACTCCGAG CAGTTTTTCC      660

AACAACTCGT CCGTGATGGG TGATCCGCTG ATCGACGCCA ATACCGGTCC CGGTGACAGC      720

GGCAATACCC GTGGTGAAGC GGGGCAACTG ATCGGCGAGC TTATCGACCG TGGCCTGCAA      780

TCGGTATTGG CCGGTGGTGG ACTGGGCACA CCCGTAAACA CCCCGCAGAC CGGTACGTCG      840

GCGAATGGCG GACAGTCCGC TCAGGATCTT GATCAGTTGC TGGGCGGCTT GCTGCTCAAG      900

GGCCTGGAGG CAACGCTCAA GGATGCCGGG CAAACAGGCA CCGACGTGCA GTCGAGCGCT      960

GCGCAAATCG CCACCTTGCT GGTCAGTACG CTGCTGCAAG GCACCCGCAA TCAGGCTGCA     1020

GCCTGA                                                                1026
```

(2) INFORMATION FOR SEQ ID NO:7:

(i) SEQUENCE CHARACTERISTICS:
        (A) LENGTH: 344 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Ser Val Gly Asn Ile Gln Ser Pro Ser Asn Leu Pro Gly Leu Gln
 1               5                  10                  15

Asn Leu Asn Leu Asn Thr Asn Thr Asn Ser Gln Gln Ser Gly Gln Ser
             20                  25                  30

Val Gln Asp Leu Ile Lys Gln Val Glu Lys Asp Ile Leu Asn Ile Ile
         35                  40                  45

Ala Ala Leu Val Gln Lys Ala Gln Ser Ala Gly Asn Thr Gly
     50                  55                  60

Asn Thr Gly Asn Ala Pro Ala Lys Asp Gly Asn Ala Asn Ala Gly Ala
 65                  70                  75                  80

Asn Asp Pro Ser Lys Asn Asp Pro Ser Lys Ser Gln Ala Pro Gln Ser
                 85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240
```

```
Gln Gly Gly Leu Thr Gly Val Leu Gln Lys Leu Met Lys Ile Leu Asn
                245                 250                 255

Ala Leu Val Gln Met Met Gln Gln Gly Leu Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
        290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

(2) INFORMATION FOR SEQ ID NO:8:

(i) SEQUENCE CHARACTERISTICS:
        (A) LENGTH: 1035 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
ATGTCAGTCG GAAACATCCA GAGCCCGTCG AACCTCCCGG GTCTGCAGAA CCTGAACCTC    60

AACACCAACA CCAACAGCCA GCAATCGGGC CAGTCCGTGC AAGACCTGAT CAAGCAGGTC   120

GAGAAGGACA TCCTCAACAT CATCGCAGCC CTCGTGCAGA AGGCCGCACA GTCGGCGGGC   180

GGCAACACCG GTAACACCGG CAACGCGCCG GCGAAGGACG GCAATGCCAA CGCGGGCGCC   240

AACGACCCGA GCAAGAACGA CCCGAGCAAG AGCCAGGCTC CGCAGTCGGC CAACAAGACC   300

GGCAACGTCG ACGACGCCAA CAACCAGGAT CCGATGCAAG CGCTGATGCA GCTGCTGGAA   360

GACCTGGTGA AGCTGCTGAA GGCGGCCCTG CACATGCAGC AGCCCGGCGG CAATGACAAG   420

GGCAACGGCG TGGGCGGTGC CAACGGCGCC AAGGGTGCCG GCGGCCAGGG CGGCCTGGCC   480

GAAGCGCTGC AGGAGATCGA GCAGATCCTC GCCCAGCTCG GCGGCGGCGG TGCTGGCGCC   540

GGCGGCGCGG GTGGCGGTGT CGGCGGTGCT GGTGGCGCGG ATGGCGGCTC CGGTGCGGGT   600

GGCGCAGGCG GTGCGAACGG CGCCGACGGC GGCAATGGCG TGAACGGCAA CCAGGCGAAC   660

GGCCCGCAGA ACGCAGGCGA TGTCAACGGT GCCAACGGCG CGGATGACGG CAGCGAAGAC   720

CAGGGCGGCC TCACCGGCGT GCTGCAAAAG CTGATGAAGA TCCTGAACGC GCTGGTGCAG   780

ATGATGCAGC AAGGCGGCCT CGGCGGCGGC AACCAGGCGC AGGGCGGCTC GAAGGGTGCC   840

GGCAACGCCT CGCCGGCTTC CGGCGCGAAC CCGGGCGCGA ACCAGCCCGG TTCGGCGGAT   900

GATCAATCGT CCGGCCAGAA CAATCTGCAA TCCCAGATCA TGGATGTGGT GAAGGAGGTC   960

GTCCAGATCC TGCAGCAGAT GCTGGCGGCG CAGAACGGCG GCAGCCAGCA GTCCACCTCG  1020

ACGCAGCCGA TGTAA                                                  1035
```

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS:
        (D) TOPOLOGY: linear -continued

```
    (ii) MOLECULE TYPE: protein (xi) SEQUENCE DESCRIPTION: SEQ ID NO:9:

Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25

(2) INFORMATION FOR SEQ ID NO:10:

(i) SEQUENCE CHARACTERISTICS:
         (A) LENGTH: 20 amino acids
         (B) TYPE: amino acid
         (C) STRANDEDNESS:
         (D) TOPOLOGY: linear (ii) MOLECULE TYPE: protein (xi) SEQUENCE DESCRIPTION: SEQ ID NO:10:

Ser Ser Gln Gln Ser Pro Ser Ala Gly Ser Glu Gln Gln Leu Asp Gln
1               5                   10                  15

Leu Leu Ala Met
            20
```